United States Patent
Su et al.

(10) Patent No.: US 10,323,244 B2
(45) Date of Patent: Jun. 18, 2019

(54) LNCRNA AND ONCOLYTIC ADENOVIRUS, AND APPLICATION THEREOF

(71) Applicant: SECOND MILITARY MEDICAL UNIVERSITY OF THE PEOPLE'S LIBERATION ARMY, Shanghai (CN)

(72) Inventors: Changqing Su, Shanghai (CN); Yinghan Su, Shanghai (CN); Xiaoya Li, Shanghai (CN); Weidan Ji, Shanghai (CN); Kouyong Liu, Shanghai (CN)

(73) Assignee: SECOND MILITARY MEDICAL UNIVERSITY OF THE PEOPLE'S LIBERATION ARMY, Shanghai (CN)

( * ) Notice: Subject to any disclaimer, the term of this patent is extended or adjusted under 35 U.S.C. 154(b) by 0 days.

(21) Appl. No.: 15/523,422

(22) PCT Filed: Oct. 14, 2015

(86) PCT No.: PCT/CN2015/091892
§ 371 (c)(1),
(2) Date: May 1, 2017

(87) PCT Pub. No.: WO2016/124002
PCT Pub. Date: Aug. 11, 2016

(65) Prior Publication Data
US 2017/0314018 A1  Nov. 2, 2017

(30) Foreign Application Priority Data

Feb. 4, 2015 (CN) .......................... 2015 1 0056926

(51) Int. Cl.
| | | |
|---|---|---|
| *C12N 15/11* | (2006.01) | |
| *C12N 15/113* | (2010.01) | |
| *A61K 31/7088* | (2006.01) | |
| *A61K 35/761* | (2015.01) | |
| *A61K 49/00* | (2006.01) | |
| *C12N 7/00* | (2006.01) | |
| *G01N 33/50* | (2006.01) | |

(52) U.S. Cl.
CPC ........ *C12N 15/113* (2013.01); *A61K 31/7088* (2013.01); *A61K 35/761* (2013.01); *A61K 49/0008* (2013.01); *C12N 7/00* (2013.01); *G01N 33/5011* (2013.01); *C12N 2310/113* (2013.01); *C12N 2310/14* (2013.01); *C12N 2310/20* (2017.05); *C12N 2320/32* (2013.01); *C12N 2710/10021* (2013.01); *C12N 2710/10032* (2013.01); *C12N 2710/10043* (2013.01)

(58) Field of Classification Search
None
See application file for complete search history.

(56) References Cited

U.S. PATENT DOCUMENTS

2015/0329858 A1  11/2015  Aburatani et al.

FOREIGN PATENT DOCUMENTS

| CN | 104651364 A | 5/2015 |
| WO | 2013134558 A1 | 9/2013 |
| WO | 2014077354 A1 | 5/2014 |

OTHER PUBLICATIONS

Huang Jin Lan et al., "Characteristics of long non-coding RNA and its relation to hepatocellular carcinoma", Carcinogenesis vol. 35, No. 3 pp. 507-514, Feb. 6, 2014.

Yang, Hui et al. "Induction of the liver Cancer-Down-Regulated Long Noncoding RNA Uc002mbe.2 Mediates Trichostatin-Induced Apoptosis of Liver Cancer Cells" Biochemical Pharmacology, May 1, 2013.

International Search Report and Written Opinion_Translation of ISR and Written Opinion, dated Feb. 2, 2016.

*Primary Examiner* — Celine X Qian
(74) *Attorney, Agent, or Firm* — Banner & Witcoff, Ltd.

(57) ABSTRACT

Provided are an LncRNA and oncolytic adenovirus, and application thereof. The oncolytic adenovirus is used as a carrier to express the LncRNA, so as to express the LncRNA in a cancer cell; competitively binding a target gene of OncomiRs, and consuming the OncomiRs, thus protecting a cancer suppressor gene from interference and suppression of the OncomiRs, and achieving target intervention therapy of the cancer cell.

Figure 1:
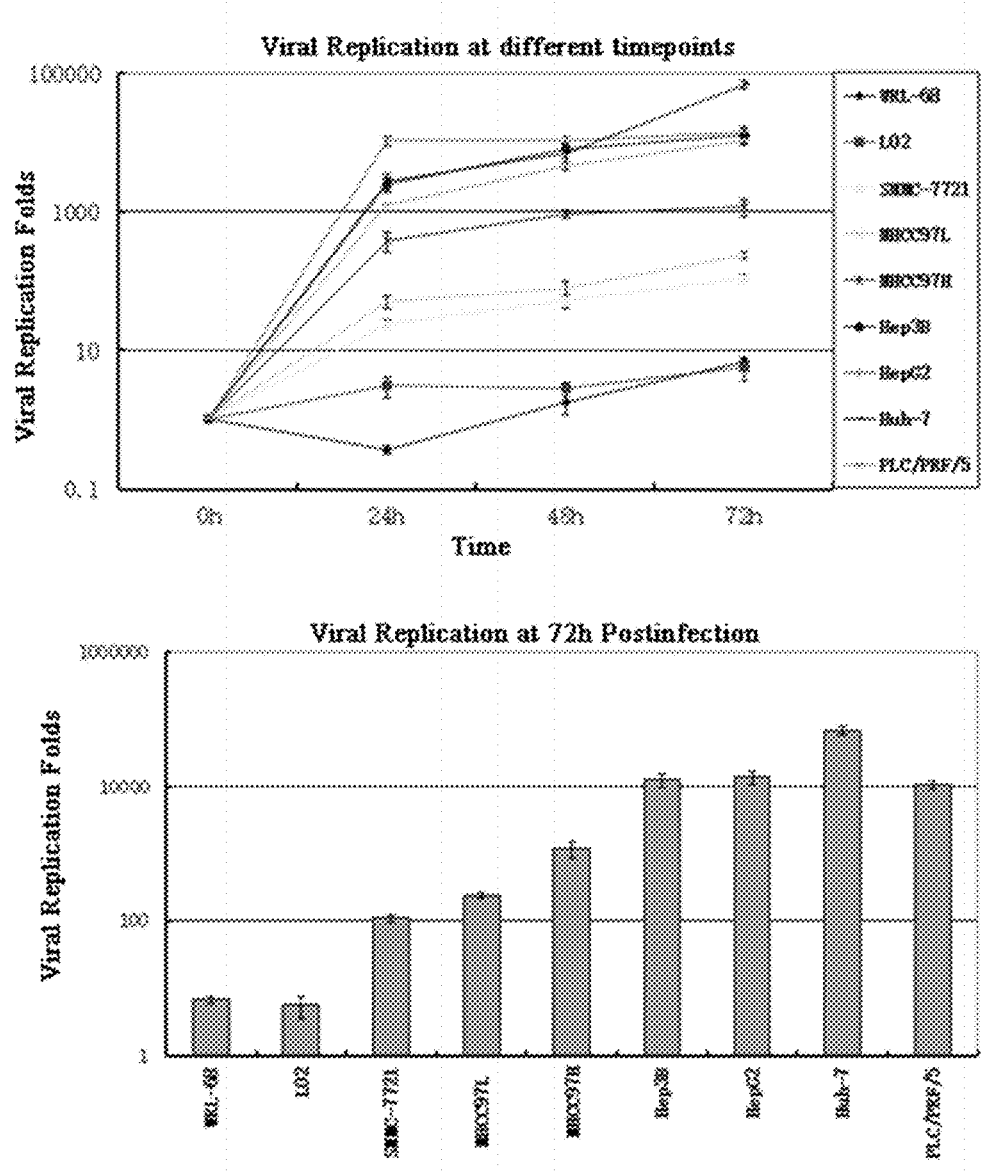

9 Claims, 6 Drawing Sheets
Specification includes a Sequence Listing.

```
                         SEQUENCE LISTING

<160> NUMBER OF SEQ ID NOS: 21

<210> SEQ ID NO 1
<211> LENGTH: 196
<212> TYPE: DNA
<213> ORGANISM: Artificial
<220> FEATURE:
<223> OTHER INFORMATION: LncRNA coding sequence

<400> SEQUENCE: 1
ctgcactgtc agcactttag cagacaatgt agctaacaat acactgccat acttctttac      60
attccaaatt cggttctaca gggtcagtct gataagctat cacgattagc attatcagtt     120
ctccgtcctg cactgtaagc actttagact gtgagctcct cgaaccacta gtgacttcac     180
cgacagcaat gaatgt                                                     196

<210> SEQ ID NO 2
<211> LENGTH: 1176
<212> TYPE: DNA
<213> ORGANISM: Artificial
<220> FEATURE:
<223> OTHER INFORMATION: LncRNA coding sequence

<400> SEQUENCE: 2
ctgcactgtc agcactttag cagacaatgt agctaacaat acactgccat acttctttac      60
attccaaatt cggttctaca gggtcagtct gataagctat cacgattagc attatcagtt     120
ctccgtcctg cactgtaagc actttagact gtgagctcct cgaaccacta gtgacttcac     180
cgacagcaat gaatgtctgc actgtcagca ctttagcaga caatgtagct aacaatacac     240
tgccatactt ctttacattc caaattcggt tctacagggt cagtctgata agctatcacg     300
attagcatta tcagttctcc gtcctgcact gtaagcactt tagactgtga gctcctcgaa     360
ccactagtga cttcaccgac agcaatgaat gtctgcactg tcagcacttt agcagacaat     420
gtagctaaca atacactgcc atacttcttt acattccaaa ttcggttcta cagggtcagt     480
ctgataagct atcacgatta gcattatcag ttctccgtcc tgcactgtaa gcactttaga     540
ctgtgagctc ctcgaaccac tagtgacttc accgacagca atgaatgtct gcactgtcag     600
cactttagca gacaatgtag ctaacaatac actgccatac ttctttacat tccaaattcg     660
gttctacagg gtcagtctga taagctatca cgattagcat tatcagttct ccgtcctgca     720
ctgtaagcac tttagactgt gagctcctcg aaccactagt gacttcaccg acagcaatga     780
```

```
atgtctgcac tgtcagcact ttagcagaca atgtagctaa caatacactg ccatacttct    840
ttacattcca aattcggttc tacagggtca gtctgataag ctatcacgat tagcattatc    900
agttctccgt cctgcactgt aagcacttta gactgtgagc tcctcgaacc actagtgact    960
tcaccgacag caatgaatgt ctgcactgtc agcactttag cagacaatgt agctaacaat   1020
acactgccat acttctttac attccaaatt cggttctaca gggtcagtct gataagctat   1080
cacgattagc attatcagtt ctccgtcctg cactgtaagc actttagact gtgagctcct   1140
cgaaccacta gtgacttcac cgacagcaat gaatgt                             1176

<210> SEQ ID NO 3
<211> LENGTH: 1186
<212> TYPE: DNA
<213> ORGANISM: Artificial
<220> FEATURE:
<223> OTHER INFORMATION: LncRNA coding sequence

<400> SEQUENCE: 3
caccatgcct gcactgtcag cactttagca gacaatgtag ctaacaatac actgccatac     60
ttctttacat tccaaattcg gttctacagg gtcagtctga taagctatca cgattagcat    120
tatcagttct ccgtcctgca ctgtaagcac tttagactgt gagctcctcg aaccactagt    180
gacttcaccg acagcaatga atgtctgcac tgtcagcact ttagcagaca atgtagctaa    240
caatacactg ccatacttct ttacattcca aattcggttc tacagggtca gtctgataag    300
ctatcacgat tagcattatc agttctccgt cctgcactgt aagcacttta gactgtgagc    360
tcctcgaacc actagtgact tcaccgacag caatgaatgt ctgcactgtc agcactttag    420
cagacaatgt agctaacaat acactgccat acttctttac attccaaatt cggttctaca    480
gggtcagtct gataagctat cacgattagc attatcagtt ctccgtcctg cactgtaagc    540
actttagact gtgagctcct cgaaccacta gtgacttcac cgacagcaat gaatgtctgc    600
actgtcagca ctttagcaga caatgtagct aacaatacac tgccatactt ctttacattc    660
caaattcggt tctacagggt cagtctgata agctatcacg attagcatta tcagttctcc    720
gtcctgcact gtaagcactt tagactgtga gctcctcgaa ccactagtga cttcaccgac    780
agcaatgaat gtctgcactg tcagcacttt agcagacaat gtagctaaca atacactgcc    840
atacttcttt acattccaaa ttcggttcta cagggtcagt ctgataagct atcacgatta    900
gcattatcag ttctccgtcc tgcactgtaa gcactttaga ctgtgagctc ctcgaaccac    960
tagtgacttc accgacagca atgaatgtct gcactgtcag cactttagca gacaatgtag   1020
ctaacaatac actgccatac ttctttacat tccaaattcg gttctacagg gtcagtctga   1080
taagctatca cgattagcat tatcagttct ccgtcctgca ctgtaagcac tttagactgt   1140
gagctcctcg aaccactagt gacttcaccg acagcaatga atgtag                  1186

<210> SEQ ID NO 4
<211> LENGTH: 196
<212> TYPE: RNA
<213> ORGANISM: Artificial
<220> FEATURE:
<223> OTHER INFORMATION: LncRNA sequence

<400> SEQUENCE: 4
cugcacuguc agcacuuuag cagacaaugu agcuaacaau acacugccau acuucuuuac     60
auuccaaauu cgguucuaca gggucagucu gauaagcuau cacgauuagc auuaucaguu    120
```

| | |
|---|---|
| cuccguccug cacuguaagc acuuuagacu gugagcuccu cgaaccacua gugacuucac | 180 |
| cgacagcaau gaaugu | 196 |

<210> SEQ ID NO 5
<211> LENGTH: 1176
<212> TYPE: RNA
<213> ORGANISM: Artificial
<220> FEATURE:
<223> OTHER INFORMATION: LncRNA sequence

<400> SEQUENCE: 5

| | |
|---|---|
| cugcacuguc agcacuuuag cagacaaugu agcuaacaau acacugccau acuucuuuac | 60 |
| auuccaaauu cgguucuaca ggucagucu gauaagcuau cacgauuagc auuaucaguu | 120 |
| cuccguccug cacuguaagc acuuuagacu gugagcuccu cgaaccacua gugacuucac | 180 |
| cgacagcaau gaaugucugc acugucagca cuuuagcaga caaguagcu aacaauacac | 240 |
| ugccauacuu cuuuacauuc caaauucggu ucuacagggu cagucugaua agcuaucacg | 300 |
| auuagcauua ucaguucucc guccugcacu guaagcacuu uagacuguga gcuccucgaa | 360 |
| ccacuaguga cuuccaccgac agcaaugaau gucugcacug ucagcacuuu agcagacaau | 420 |
| guagcuaaca auacacugcc auacuucuuu acauuccaaa uucgguucua cagggucagu | 480 |
| cugauaagcu aucacgauua gcauuaucag uucccgucc ugcacuguaa gcacuuuaga | 540 |
| cugugagcuc cucgaaccac uagugacuuc accgacagca augaaugucu gcacugucag | 600 |
| cacuuuagca gacaaugual cuaacaauac acugccauac uucuuuacau uccaaauucg | 660 |
| guucuacagg gucagucuga uaagcuauca cgauuagcau uaucaguucu ccguccugca | 720 |
| cuguaagcac uuuagacugu gagcuccucg aaccacuagu gacuuccacg acagcaauga | 780 |
| augucugcac ugucagcacu uuagcagaca auguagcuaa caauacacug ccauacuucu | 840 |
| uuacauucca aauucgguuc uacagggucà gucugauaag cuaucacgau uagcauuauc | 900 |
| aguucuccgu ccugcacugu aagcacuuua gacugugagc uccucgaacc acuagugacu | 960 |
| ucaccgacag caaugaaugu cugcacuguc agcacuuuag cagacaaugu agcuaacaau | 1020 |
| acacugccau acuucuuuac auuccaaauu cgguucuaca ggucagucu gauaagcuau | 1080 |
| cacgauuagc auuaucaguu cuccguccug cacguuaagc acuuuagacu gugagcuccu | 1140 |
| cgaaccacua gugacuucac cgacagcaau gaaugu | 1176 |

<210> SEQ ID NO 6
<211> LENGTH: 531
<212> TYPE: DNA
<213> ORGANISM: Artificial
<220> FEATURE:
<223> OTHER INFORMATION: CMV promoter

<400> SEQUENCE: 6

| | |
|---|---|
| gatatactga gtcattaggg actttccaat gggttttgcc cagtacataa ggtcaatagg | 60 |
| ggtgaatcaa caggaaagtc ccattggagc caagtacact gagtcaatag gactttcca | 120 |
| ttgggttttg cccagtacaa aaggtcaata gggggtgagt caatgggttt tcccattat | 180 |
| tggcacgtac ataaggtcaa taggggtgag tcattgggtt tttccagcca tttaattaaa | 240 |
| acgccatgta ctttcccacc attgacgtca atgggctatt gaaactaatg caacgtgacc | 300 |
| tttaaacggt actttcccat agctgattaa tgggaaagta ccgttctcga gccaatacac | 360 |
| gtcaatggga agtgaaaggg cagccaaaac gtaacaccgc ccggttttc cctggaaat | 420 |
| tccatattgg cactcattct attggctgag ctgcgttcta cgtgggtata agaggcgcga | 480 | ccagcgtcgg taccgtcgca gtcttcggtc tgaccaccgt agaacgcaga t        531

<210> SEQ ID NO 7
<211> LENGTH: 990
<212> TYPE: DNA
<213> ORGANISM: Artificial
<220> FEATURE:
<223> OTHER INFORMATION: Survivin promoter

<400> SEQUENCE: 7
cggctagcca tagaaccaga gaagtgagtg gatgtgatgc ccagctccag aagtgactcc     60
agaacaccct gttccaaagc agaggacaca ctgatttttt ttttaatagg ctgcaggact   120
tactgttggt gggacgccct gctttgcgaa gggaaggag gagtttgccc tgagcacagg    180
ccccaccct ccactgggct tccccagct cccttgtctt cttatcacgg tagtggccca     240
gtccctggcc cctgactcca gaaggtggcc ctcctggaaa cccaggtcgt gcagtcaacg   300
atgtactcgc cgggacagcg atgtctgctg cactccatcc ctcccctgtt catttgtcct   360
tcatgcccgt ctggagtaga tgcttttgc agaggtggca ccctgtaaag ctctcctgtc    420
tgactttttt tttttttag actgagtttt gctcttgttg cctaggctgg agtgcaatgg    480
cacaatctca gctcactgca ccctctgcct cccgggttca gcgattctc ctgcctcagc    540
ctcccgagta gttgggatta caggcatgca ccaccacgcc cagctaattt ttgtattttt   600
agtagagaca aggtttcacc gtgatggcca ggctggtctt gaactccagg actcaagtga   660
tgctcctgcc taggcctctc aaagtgttgg gattacaggc gtgagccact gcacccggcc   720
tgcacgcgtt cttgaaagc agtcgagggg gcgctaggtg tgggcaggga cgagctggcg    780
cggcgtcgct gggtgcaccg cgaccacggg cagagccacg cggcgggagg actacaactc   840
ccggcacacc ccgcgccgcc ccgcctctac tcccagaagg ccgcggggg tggaccgcct    900
aagagggcgt gcgctcccga catgccccgc ggcgcgccat taaccgccag atttgaatcg   960
cgggacccgt tggcagaggt ggagatcttc                                    990

<210> SEQ ID NO 8
<211> LENGTH: 986
<212> TYPE: DNA
<213> ORGANISM: Artificial
<220> FEATURE:
<223> OTHER INFORMATION: E1a sequence

<400> SEQUENCE: 8
atgagacata ttatctgcca cggaggtgtt attaccgaag aaatggccgc cagtcttttg     60
gaccagctga tcgaagaggt actggctgat aatcttccac ctcctagcca ttttgaacca   120
cctacccttc acgaactgta tgatttagac gtgacggccc cgaagatcc caacgaggag    180
gcggtttcgc agatttttcc cgactctgta atgttggcgg tgcaggaagg gattgactta   240
ctcactttc cgccggcgcc cggttctccg gagccgcctc acctttcccg gcagcccgag    300
cagccggagc agagagcctt gggtccggtt tctatgccaa accttgtacc ggaggtgatc   360
gatcttacct gccacgaggc tggctttcca cccagtgacg acgaggatga agagggtgag   420
gagtttgtgt tagattatgt ggagcacccc ggcacggtt gcaggtcttg tcattatcac    480
cggaggaata cggggaccc agatattatg tgttcgcttt gctatatgag gacctgtggc    540
atgtttgtct acagtaagtg aaaattatgg gcagtgggtg atagagtggt gggtttggtg   600
tggtaatttt ttttttaatt tttacagttt tgtggtttaa agaattttgt attgtgattt    660

| | |
|---|---|
| ttttaaaagg tcctgtgtct gaacctgagc ctgagcccga gccagaaccg gagcctgcaa | 720 |
| gacctacccg ccgtcctaaa atggcgcctg ctatcctgag acgcccgaca tcacctgtgt | 780 |
| ctagagaatg caatagtagt acggatagct gtgactccgg tccttctaac acacctcctg | 840 |
| agatacaccc ggtggtcccg ctgtgcccca ttaaaccagt tgccgtgaga gttggtgggc | 900 |
| gtcgccaggc tgtggaatgt atcgaggact tgcttaacga gcctgggcaa cctttggact | 960 |
| tgagctgtaa acgccccagg ccataa | 986 |

<210> SEQ ID NO 9
<211> LENGTH: 4196
<212> TYPE: DNA
<213> ORGANISM: Artificial
<220> FEATURE:
<223> OTHER INFORMATION: recombinant region in the recombinant oncolytic
      adenovirus

<400> SEQUENCE: 9

| | |
|---|---|
| tctagacggc tagccataga accagagaag tgagtggatg tgatgcccag ctccagaagt | 60 |
| gactccagaa caccctgttc caaagcagag gacacactga tttttttttt aataggctgc | 120 |
| aggacttact gttggtggga cgccctgctt tgcgaaggga aaggaggagt ttgccctgag | 180 |
| cacaggcccc caccctccac tgggcttttc ccagctccct tgtcttctta tcacggtagt | 240 |
| ggcccagtcc ctggccctg actccagaag gtggccctcc tggaaaccca ggtcgtgcag | 300 |
| tcaacgatgt actcgccggg acagcgatgt ctgctgcact ccatccctcc cctgttcatt | 360 |
| tgtccttcat gcccgtctgg agtagatgct ttttgcagag gtggcaccct gtaaagctct | 420 |
| cctgtctgac tttttttttt ttttagactg agttttgctc ttgttgccta ggctggagtg | 480 |
| caatggcaca atctcagctc actgcaccct ctgcctcccg ggttcaagcg attctcctgc | 540 |
| ctcagcctcc cgagtagttg ggattacagg catgcaccac cacgcccagc taattttttgt | 600 |
| atttttagta gagacaaggt ttcaccgtga tggccaggct ggtcttgaac tccaggactc | 660 |
| aagtgatgct cctgcctagg cctctcaaag tgttgggatt acaggcgtga gccactgcac | 720 |
| ccggcctgca cgcgttcttt gaaagcagtc gaggggcgc taggtgtggg cagggacgag | 780 |
| ctggcgcggc gtcgctgggt gcaccgcgac cacgggcaga gccacgcggc gggaggacta | 840 |
| caactcccgg cacaccccgc gccgccccgc ctctactccc agaaggccgc gggggtgga | 900 |
| ccgcctaaga gggcgtgcgc tcccgacatg ccccgcggcg cgccattaac cgccagattt | 960 |
| gaatcgcggg accgttggc agaggtggag atcttcgaat tcaccatgag acatattatc | 1020 |
| tgccacggag gtgttattac cgaagaaatg gccgccagtc ttttggacca gctgatcgaa | 1080 |
| gaggtactgg ctgataatct tccacctcct agccattttg aaccacctac ccttcacgaa | 1140 |
| ctgtatgatt tagacgtgac ggccccgaa gatcccaacg aggaggcggt ttcgcagatt | 1200 |
| tttcccgact ctgtaatgtt ggcggtgcag gaagggattg acttactcac ttttccgccg | 1260 |
| gcgcccggtt ctccggagcc gcctcacctt tcccggcagc ccgagcagcc ggagcagaga | 1320 |
| gccttgggtc cggtttctat gccaaacctt gtaccggagg tgatcgatct tacctgccac | 1380 |
| gaggctggct ttccacccag tgacgacgag gatgaagagg gtgaggagtt tgtgttagat | 1440 |
| tatgtggagc accccgggca cggttgcagg tcttgtcatt atcaccggag aatacgggg | 1500 |
| gacccagata ttatgtgttc gctttgctat atgaggacct gtggcatgtt tgtctacagt | 1560 |
| aagtgaaaat tatgggcagt gggtgataga gtggtgggtt tggtgtggta attttttttt | 1620 |
| taattttttac agttttgtgg tttaaagaat tttgtattgt gatttttta aaggtcctg | 1680 |

-continued

```
tgtctgaacc tgagcctgag cccgagccag aaccggagcc tgcaagacct acccgccgtc    1740
ctaaaatggc gcctgctatc ctgagacgcc cgacatcacc tgtgtctaga aatgcaata     1800 gtagtacgga tagctgtgac tccggtcctt ctaacacacc tcctgagata cacccggtgg    1860
tcccgctgtg ccccattaaa ccagttgccg tgagagttgg tgggcgtcgc caggctgtgg    1920
aatgtatcga ggacttgctt aacgagcctg ggcaacctttt ggacttgagc tgtaaacgcc   1980
ccaggccata aggcctctgg ccggagctgc ctggtcccag agtggctgca ccacttccag    2040
ggtttattcc ctggtgccac cagccttcct atgggcccct agcaatgtc ttaggaaagg     2100 agatcaacat tttcaaatta gatgtttcaa ctgtgctcct gttttgtctt gaaagtggca    2160
ccagaggtgc ttctgcctgt gcagcgggtg ctgctggtaa cagtggctgc ttctctctct    2220
ctctctctct tttgggggct cattttttgct gttttgattc ccgggcttac caggtgagaa    2280
gtgagggagg acgggatccc gggatccgat atactgagtc attagggact ttccaatggg    2340
ttttgcccag tacataaggt caataggggt gaatcaacag gaaagtccca ttggagccaa    2400
gtacactgag tcaataggga cttttccattg ggttttgccc agtacaaaag gtcaataggg    2460
ggtgagtcaa tgggttttttc ccattattgg cacgtacata aggtcaatag ggtgagtca    2520 ttgggttttt ccagccattt aattaaaacg ccatgtactt tcccaccatt gacgtcaatg    2580
ggctattgaa actaatgcaa cgtgaccttt aaacggtact ttcccatagc tgattaatgg    2640
gaaagtaccg ttctcgagcc aatacacgtc aatgggaagt gaaagggcag ccaaaacgta    2700
acaccgcccc ggttttcccc tggaaattcc atattggcac tcattctatt ggctgagctg    2760
cgttctacgt gggtataaga ggcgcgacca gcgtcggtac cgtcgcagtc ttcggtctga    2820
ccaccgtaga acgcagatgt cgaccaccat gcctgcactg tcagcacttt agcagacaat    2880
gtagctaaca atacactgcc atacttcttt acattccaaa ttcggttcta cagggtcagt    2940
ctgataagct atcacgatta gcattatcag ttctccgtcc tgcactgtaa gcactttaga    3000
ctgtgagctc ctcgaaccac tagtgacttc accgacagca atgaatgtct gcactgtcag    3060
cactttagca gacaatgtag ctaacaatac actgccatac ttctttacat tccaaattcg    3120
gttctacagg tcagtctga taagctatca cgattagcat tatcagttct ccgtcctgca    3180
ctgtaagcac tttagactgt gagctcctcg aaccactagt gacttcaccg acagcaatga    3240
atgtctgcac tgtcagcact ttagcagaca atgtagctaa caatacactg ccatacttct    3300
ttacattcca aattcggttc tacagggtca gtctgataag ctatcacgat tagcattatc    3360
agttctccgt cctgcactgt aagcacttta gactgtgagc tcctcgaacc actagtgact    3420
tcaccgacag caatgaatgt ctgcactgtc agcactttag cagacaatgt agctaacaat    3480
acactgccat acttctttac attccaaatt cggttctaca gggtcagtct gataagctat    3540
cacgattagc attatcagtt ctccgtcctg cactgtaagc actttagact gtgagctcct    3600
cgaaccacta gtgacttcac cgacagcaat gaatgtctgc actgtcagca ctttagcaga    3660
caatgtagct aacaatacac tgccatactt ctttacattc caaattcggt tctacagggt    3720
cagtctgata agctatcacg attagcatta tcagttctcc gtcctgcact gtaagcactt    3780
tagactgtga gctcctcgaa ccactagtga cttcaccgac agcaatgaat gtctgcactg    3840
tcagcacttt agcagacaat gtagctaaca atacactgcc atacttcttt acattccaaa    3900
ttcggttcta cagggtcagt ctgataagct atcacgatta gcattatcag ttctccgtcc    3960
tgcactgtaa gcactttaga ctgtgagctc ctcgaaccac tagtgacttc accgacagca    4020
atgaatgtag ttcgagcaac ttgtttattg cagcttataa tggttacaaa taaagcaata    4080
```

```
gcatcacaaa tttcacaaat aaagcattt  tttcactgca ttctagttgt ggtttgtcca        4140
aactcatcaa tgtatcttat catgtctgga tcgtctagca tcgaagatcc gtcgac           4196

<210> SEQ ID NO 10
<211> LENGTH: 34441
<212> TYPE: DNA
<213> ORGANISM: Artificial
<220> FEATURE:
<223> OTHER INFORMATION: genome sequence of the recombinant oncolytic
      adenovirus

<400> SEQUENCE: 10 ttatttgga  ttgaagccaa tatgataatg agggggtgga gtttgtgacg tggcgcgggg         60
cgtgggaacg gggcgggtga cgtagtagtg tggcggaagt gtgatgttgc aagtgtggcg        120
gaacacatgt aagcgacgga tgtggcaaaa gtgacgtttt tggtgtgcgc cggtgtacac        180
aggaagtgac aattttcgcg cggtttttagg cggatgttgt agtaaatttg ggcgtaaccg       240
agtaagattt ggccattttc gcgggaaaac tgaataagag gaagtgaaat ctgaataatt       300
ttgtgttact catagcgcgt aatatttgtc tagggccgcg gggactttga ccgtttacgt       360
ggagactcgc ccaggtgttt ttctcaggtg ttttccgcgt tccgggtcaa agttggcgtt       420
ttattattat agtcagctct agacggctag ccatagaacc agagaagtga gtggatgtga       480
tgcccagctc cagaagtgac tccagaacac cctgttccaa agcagaggac acactgattt       540
tttttttaat aggctgcagg acttactgtt ggtgggacgc cctgctttgc gaagggaaag       600
gaggagtttg ccctgagcac aggccccccac cctccactgg gctttcccca gctcccttgt       660
cttcttatca cggtagtggc ccagtccctg gcccctgact ccagaaggtg gccctcctgg       720
aaacccaggt cgtgcagtca acgatgtact cgccgggaca cgcgatgtctg ctgcactcca       780 tccctcccct gttcatttgt ccttcatgcc cgtctggagt agatgctttt tgcagaggtg       840
gcaccctgta aagctctcct gtctgacttt ttttttttt  tagactgagt tttgctcttg       900
ttgcctaggc tggagtgcaa tggcacaatc tcagctcact gcaccctctg cctcccgggt       960
tcaagcgatt ctcctgcctc agcctcccga gtagttggga ttacaggcat gcaccaccac      1020
gcccagctaa ttttttgtatt tttagtagag acaaggtttc accgtgatgg ccaggctggt      1080
cttgaactcc aggactcaag tgatgctcct gcctaggcct ctcaaagtgt tgggattaca      1140
ggcgtgagcc actgcacccg gcctgcacgc gttctttgaa agcagtcgag ggggcgctag      1200
gtgtgggcag ggacgagctg gcgcggccgtc gctgggtgca ccgcgaccac gggcagagcc      1260
acgcggcggg aggactacaa ctcccggcac accccgcgcc gccccgcctc tactcccaga      1320
aggccgcggg gggtggaccg cctaagaggg cgtgcgctcc cgacatgccc cgcggcgcgc      1380
cattaaccgc cagatttgaa tcgcgggacc cgttggcaga ggtggagatc ttcgaattca      1440
ccatgagaca tattatctgc cacggaggtg ttattaccga agaaatggcc gccagtcttt      1500
tggaccagct gatcgaagag gtactggctg ataatcttcc acctcctagc cattttgaac      1560
cacctaccct tcacgaactg tatgattag acgtgacggc ccccgaagat cccaacgagg      1620 aggcggttc  gcagatttt  cccgactctg taatgttggc ggtgcaggaa gggattgact      1680 tactcactt  tccgccggcg cccggttctc cggagccgcc tcacctttcc cggcagcccg      1740
agcagccgga gcagagagcc ttgggtccgg tttctatgcc aaaccttgta ccggaggtga      1800
tcgatcttac ctgccacgag gctggctttc cacccagtga cgacgaggat gaagagggtg      1860
aggagtttgt gttagattat gtggagcacc ccgggcacgg ttgcaggtct tgtcattatc      1920
```

| | |
|---|---|
| accggaggaa tacggggggac ccagatatta tgtgttcgct ttgctatatg aggacctgtg | 1980 |
| gcatgtttgt ctacagtaag tgaaaattat gggcagtggg tgatagagtg gtgggtttgg | 2040 |
| tgtggtaatt tttttttaa ttttacagt tttgtggttt aaagaatttt gtattgtgat | 2100 |
| tttttaaaa ggtcctgtgt ctgaacctga gcctgagccc gagccagaac cggagcctgc | 2160 |
| aagacctacc cgccgtccta aaatggcgcc tgctatcctg agacgcccga catcacctgt | 2220 |
| gtctagagaa tgcaatagta gtacggatag ctgtgactcc ggtccttcta acacacctcc | 2280 |
| tgagatacac ccggtggtcc cgctgtgccc cattaaacca gttgccgtga gagttggtgg | 2340 |
| gcgtcgccag gctgtggaat gtatcgagga cttgcttaac gagcctgggc aacctttgga | 2400 |
| cttgagctgt aaacgcccca ggccataagg cctctggccg gagctgcctg gtcccagagt | 2460 |
| ggctgcacca cttccagggt ttattccctg gtgccaccag ccttcctatg gccccttag | 2520 |
| caatgtctta ggaaaggaga tcaacatttt caaattagat gtttcaactg tgctcctgtt | 2580 |
| ttgtcttgaa agtggcacca gaggtgcttc tgcctgtgca gcgggtgctg ctggtaacag | 2640 |
| tggctgcttc tctctctctc tctctcttt gggggctcat ttttgctgtt ttgattcccg | 2700 |
| ggcttaccag gtgagaagtg agggaggacg ggatcccggg atccgatata ctgagtcatt | 2760 |
| agggactttc caatgggttt tgcccagtac ataaggtcaa taggggtgaa tcaacaggaa | 2820 |
| agtcccattg gagccaagta cactgagtca atagggactt tccattgggt tttgcccagt | 2880 |
| acaaaaggtc aataggggt gagtcaatgg gttttcca ttattggcac gtacataagg | 2940 |
| tcaatagggg tgagtcattg ggttttcca gccatttaat taaaacgcca tgtactttcc | 3000 |
| caccattgac gtcaatgggc tattgaaact aatgcaacgt gaccttaaa cggtactttc | 3060 |
| ccatagctga ttaatgggaa agtaccgttc tcgagccaat acacgtcaat gggaagtgaa | 3120 |
| agggcagcca aaacgtaaca ccgccccggt ttttccctgg aaattccata ttggcactca | 3180 |
| ttctattggc tgagctgcgt tctacgtggg tataagaggc gcgaccagcg tcggtaccgt | 3240 |
| cgcagtcttc ggtctgacca ccgtagaacg cagatgtcga ccaccatgcc tgcactgtca | 3300 |
| gcactttagc agacaatgta gctaacaata cactgccata cttctttaca ttccaaattc | 3360 |
| ggttctacag ggtcagtctg ataagctatc acgattagca ttatcagttc tccgtcctgc | 3420 |
| actgtaagca ctttagactg tgagctcctc gaaccactag tgacttcacc gacagcaatg | 3480 |
| aatgtctgca ctgtcagcac tttagcagac aatgtagcta acaatacact gccatacttc | 3540 |
| tttacattcc aaattcggtt ctacagggtc agtctgataa gctatcacga ttagcattat | 3600 |
| cagttctccg tcctgcactg taagcacttt agactgtgag ctcctcgaac cactagtgac | 3660 |
| ttcaccgaca gcaatgaatg tctgcactgt cagcacttta gcagacaatg tagctaacaa | 3720 |
| tacactgcca tacttcttta cattccaaat tcggttctac agggtcagtc tgataagcta | 3780 |
| tcacgattag cattatcagt tctccgtcct gcactgtaag cactttagac tgtgagctcc | 3840 |
| tcgaaccact agtgacttca ccgacagcaa tgaatgtctg cactgtcagc actttagcag | 3900 |
| acaatgtagc taacaataca ctgccatact tctttacatt ccaaattcgg ttctacaggg | 3960 |
| tcagtctgat aagctatcac gattagcatt atcagttctc cgtcctgcac tgtaagcact | 4020 |
| ttagactgtg agctcctcga accactagtg acttcaccga cagcaatgaa tgtctgcact | 4080 |
| gtcagcactt tagcagacaa tgtagctaac aatacactgc catacttctt tacattccaa | 4140 |
| attcggttct acagggtcag tctgataagc tatcacgatt agcattatca gttctccgtc | 4200 |
| ctgcactgta agcactttag actgtgagct cctcgaacca ctagtgactt caccgacagc | 4260 |

-continued

```
aatgaatgtc tgcactgtca gcactttagc agacaatgta gctaacaata cactgccata      4320
cttctttaca ttccaaattc ggttctacag ggtcagtctg ataagctatc acgattagca      4380
ttatcagttc tccgtcctgc actgtaagca ctttagactg tgagctcctc gaaccactag      4440
tgacttcacc gacagcaatg aatgtagttc gagcaacttg tttattgcag cttataatgg      4500
ttacaaataa agcaatagca tcacaaattt cacaaataaa gcattttttt cactgcattc      4560
tagttgtggt ttgtccaaac tcatcaatgt atcttatcat gtctggatcg tctagcatcg      4620
aagatccgtc gacaataact tcgtatagca tacattatac gaagttataa gtactgaatt      4680
cggatctggg cgtggttaag ggtgggaaag aatatataag gtgggggtct tatgtagttt      4740
tgtatctgtt ttgcagcagc cgccgccgcc atgagcacca actcgtttga tggaagcatt      4800
gtgagctcat atttgacaac gcgcatgccc ccatgggccg gggtgcgtca gaatgtgatg      4860
ggctccagca ttgatggtcg ccccgtcctg cccgcaaact ctactacctt gacctacgag      4920
accgtgtctg gaacgccgtt ggagactgca gcctccgccg ccgcttcagc cgctgcagcc      4980
accgcccgcg ggattgtgac tgactttgct ttcctgagcc cgcttgcaag cagtgcagct      5040
tcccgttcat ccgcccgcga tgacaagttg acggctcttt tggcacaatt ggattctttg      5100
acccgggaac ttaatgtcgt ttctcagcag ctgttggatc tgcgccagca ggtttctgcc      5160
ctgaaggctt cctcccctcc caatgcggtt taaaacataa ataaaaaacc agactctgtt      5220
tggatttgga tcaagcaagt gtcttgctgt ctttatttag gggttttgcg cgcgcggtag      5280
gcccgggacc agcggtctcg gtcgttgagg gtcctgtgta ttttttccag gacgtggtaa      5340
aggtgactct ggatgttcag atacatgggc ataagcccgt ctctggggtg gaggtagcac      5400
cactgcagag cttcatgctg cggggtggtg ttgtagatga tccagtcgta gcaggagcgc      5460
tgggcgtggt gcctaaaaat gtcttttcagt agcaagctga ttgccagggg caggcccttg      5520
gtgtaagtgt ttacaaagcg gttaagctgg gatgggtgca tacgtgggga tatgagatgc      5580
atcttggact gtattttag gttggctatg ttcccagcca tatccctccg ggattcatg       5640 ttgtgcagaa ccaccagcac agtgtatccg gtgcacttgg gaaatttgtc atgtagctta      5700
gaaggaaatg cgtggaagaa cttggagacg cccttgtgac ctccaagatt ttccatgcat      5760
tcgtccataa tgatggcaat gggcccacgg gcggcggcct gggcgaagat atttctggga      5820
tcactaacgt catagttgtg ttccaggatg agatcgtcat aggccatttt tacaaagcgc      5880
gggcggaggg tgccagactg cggtataatg gttccatccg gcccaggggc gtagttaccc      5940
tcacagattt gcatttccca cgctttgagt tcagatgggg ggatcatgtc tacctgcggg      6000
gcgatgaaga aaacggtttc cggggtaggg gagatcagct gggaagaaag caggttcctg      6060
agcagctgcg acttaccgca gccggtgggc ccgtaaatca cacctattac cgggtgcaac      6120
tggtagttaa gagagctgca gctgccgtca tccctgagca gggggggccac ttcgttaagc      6180 atgtccctga ctcgcatgtt ttccctgacc aaatccgcca gaaggcgctc gccgcccagc      6240
gatagcagtt cttgcaagga agcaaagttt ttcaacggtt tgagaccgtc cgccgtaggc      6300
atgcttttga gcgtttgacc aagcagttcc aggcggtccc acagctcggt cacctgctct      6360
acggcatctc gatccagcat atctcctcgt ttcgcgggtt ggggcggctt tcgctgtacg      6420
gcagtagtcg gtgctcgtcc agacgggcca gggtcatgtc tttccacggg cgcagggtcc      6480
tcgtcagcgt agtctgggtc acggtgaagg ggtgcgctcc gggctgcgcg ctggccaggg      6540
tgcgcttgag gctggtcctg ctggtgctga agcgctgccg gtcttcgccc tgcgcgtcgg      6600
ccaggtagca tttgaccatg gtgtcatagt ccagcccctc cgcggcgtgg cccttggcgc      6660
```

```
gcagcttgcc cttggaggag gcgccgcacg aggggcagtg cagacttttg agggcgtaga      6720
gcttgggcgc gagaaatacc gattccgggg agtaggcatc cgcgccgcag gccccgcaga      6780
cggtctcgca ttccacgagc caggtgagct ctggccgttc ggggtcaaaa accaggtttc      6840
ccccatgctt tttgatgcgt ttcttacctc tggtttccat gagccggtgt ccacgctcgg      6900
tgacgaaaag gctgtccgtg tccccgtata cagacttgag aggcctgtcc tcgagcggtg      6960
ttccgcggtc ctcctcgtat agaaactcgg accactctga dacaaaggct cgcgtccagg      7020
ccagcacgaa ggaggctaag tgggaggggt agcggtcgtt gtccactagg gggtccactc      7080
gctccagggt gtgaagacac atgtcgccct cttcggcatc aaggaaggtg attggtttgt      7140
aggtgtaggc cacgtgaccg ggtgttcctg aaggggggct ataaaagggg gtggggcgc       7200 gttcgtcctc actctcttcc gcatcgctgt ctgcgagggc cagctgttgg ggtgagtact      7260
ccctctgaaa agcgggcatg acttctgcgc taagattgtc agtttccaaa aacgaggagg      7320
atttgatatt cacctggccc gcggtgatgc ctttgagggt ggccgcatcc atctggtcag      7380
aaaagacaat cttttgttg tcaagcttgg tggcaaacga cccgtagagg gcgttggaca       7440
gcaacttggc gatggagcgc agggtttggt ttttgtcgcg atcggcgcgc tccttggccg      7500
cgatgtttag ctgcacgtat tcgcgcgcaa cgcaccgcca ttcgggaaag acggtggtgc      7560
gctcgtcggg caccaggtgc acgcgccaac cgcggttgtg cagggtgaca aggtcaacgc      7620
tggtggctac ctctccgcgt aggcgctcgt tggtccagca gaggcggccg cccttgcgcg      7680
agcagaatgg cggtaggggg tctagctgcg tctcgtccgg ggggtctgcg tccacggtaa      7740
agaccccggg cagcaggcgc gcgtcgaagt agtctatctt gcatccttgc aagtctagcg      7800
cctgctgcca tgcgcgggcg gcaagcgcgc gctcgtatgg gttgagtggg ggaccccatg      7860
gcatggggtg ggtgagcgcg gaggcgtaca tgccgcaaat gtcgtaaacg tagagggct       7920 ctctgagtat tccaagatat gtagggtagc atcttccacc gcggatgctg gcgcgcacgt      7980
aatcgtatag ttcgtgcgag ggagcgagga ggtcgggacc gaggttgcta cgggcgggct      8040
gctctgctcg gaagactatc tgcctgaaga tggcatgtga gttggatgat atggttggac      8100
gctggaagac gttgaagctg gcgtctgtga gacctaccgc gtcacgcacg aaggaggcgt      8160
aggagtcgcg cagcttgttg accagctcgg cggtgacctg cacgtctagg gcgcagtagt      8220
ccagggtttc cttgatgatg tcatacttat cctgtccctt tttttccac agctcgcggt       8280 tgaggacaaa ctcttcgcgg tcttttccagt actcttggat cggaaacccg tcggcctccg     8340
aacggtaaga gcctagcatg tagaactggt tgacggcctg gtaggcgcag catccctttt      8400
ctacgggtag cgcgtatgcc tgcgcggcct tccggagcga ggtgtgggtg agcgcaaagg      8460
tgtccctgac catgactttg aggtactggt atttgaagtc agtgtcgtcg catccgccct      8520
gctcccagag caaaaagtcc gtgcgctttt tggaacgcgg atttggcagg gcgaaggtga      8580
catcgttgaa gagtatcttt cccgcgcgag gcataaagtt gcgtgtgatg cggaagggtc      8640
ccggcacctc ggaacggttg ttaattacct gggcggcgag cacgatctcg tcaaagccgt      8700
tgatgttgtg gcccacaatg taaagttcca agaagcgcgg gatgcccttg atggaaggca      8760
attttttaag ttcctcgtag gtgagctctt caggggagct gagcccgtgc tctgaaaggg      8820
cccagtctgc aagatgaggg ttggaagcga cgaatgagct ccacaggtca cgggccatta     8880
gcatttgcag gtggtcgcga aaggtcctaa actggcgacc tatggccatt ttttctgggg     8940
tgatgcagta gaaggtaagc gggtcttgtt cccagcggtc ccatccaagg ttcgcggcta     9000
```

```
ggtctcgcgc ggcagtcact agaggctcat ctccgccgaa cttcatgacc agcatgaagg    9060
gcacgagctg cttcccaaag gcccccatcc aagtataggt ctctacatcg taggtgacaa    9120
agagacgctc ggtgcgagga tgcgagccga tcgggaagaa ctggatctcc cgccaccaat    9180
tggaggagtg gctattgatg tggtgaaagt agaagtccct gcgacgggcc gaacactcgt    9240
gctggctttt gtaaaaacgt gcgcagtact ggcagcggtg cacgggctgt acatcctgca    9300
cgaggttgac ctgacgaccg cgcacaagga agcagagtgg gaatttgagc ccctcgcctg    9360
gcgggtttgg ctggtggtct tctacttcgg ctgcttgtcc ttgaccgtct ggctgctcga    9420
ggggagttac ggtggatcgg accaccacgc cgcgcgagcc caaagtccag atgtccgcgc    9480
gcggcggtcg gagcttgatg caacatcgc gcagatggga gctgtccatg gtctggagct    9540
cccgcggcgt caggtcaggc gggagctcct gcaggtttac ctcgcataga cgggtcaggg    9600
cgcgggctag atccaggtga tacctaatt ccaggggctg gttggtggcg cgtcgatgg    9660 cttgcaagag gccgcatccc cgcggcgcga ctacggtacc gcgcggcggg cggtgggccg    9720 cggggggtgtc cttggatgat gcatctaaaa gcggtgacgc gggcgagccc ccggaggtag    9780
ggggggctcc ggacccgccg ggagaggggg caggggcacg tcggcgccgc gcgcgggcag    9840
gagctggtgc tgcgcgcgta ggttgctggc gaacgcgacg acgcggcggt tgatctcctg    9900
aatctggcgc ctctgcgtga agacgacggg cccggtgagc ttgagcctga aagagagttc    9960
gacagaatca atttcggtgt cgttgacggc ggcctggcgc aaaatctcct gcacgtctcc   10020
tgagttgtct tgataggcga tctcggccat gaactgctcg atctcttcct cctggagatc   10080
tccgcgtccg gctcgctcca cggtggcggc gaggtcgttg gaaatgcggg ccatgagctg   10140
cgagaaggcg ttgaggcctc cctcgttcca gacgcggctg tagaccacgc ccccttcggc   10200
atcgcgggcg cgcatgacca cctgcgcgag attgagctcc acgtgccggg cgaagacggc   10260
gtagtttcgc aggcgctgaa agaggtagtt gagggtggtg gcggtgtgtt ctgccacgaa   10320
gaagtacata acccagcgtc gcaacgtgga ttcgttgata tccccaagg cctcaaggcg   10380 ctccatggcc tcgtagaagt ccacggcgaa gttgaaaaac tgggagttgc gcgccgacac   10440
ggttaactcc tcctccagaa gacggatgag ctcggcgaca gtgtcgcgca cctcgcgctc   10500
aaaggctaca ggggcctctt cttcttcttc aatctcctct tccataaggg cctcccttc   10560 ttcttcttct ggcggcggtg ggggagggg gacacggcgg cgacgacggc gcaccggag   10620 gcggtcgaca aagcgctcga tcatctcccc gcggcgacgg cgcatggtct cggtgacggc   10680
gcggccgttc tcgcggggc gcagttggaa gacgccgccc gtcatgtccc ggttatgggt   10740 tggcggggg ctgccatgcg gcagggatac ggcgctaacg atgcatctca acaattgttg   10800
tgtaggtact ccgccgccga gggacctgag cgagtccgca tcgaccggat cggaaaacct   10860
ctcgagaaag gcgtctaacc agtcacagtc gcaaggtagg ctgagcaccg tggcgggcgg   10920
cagcgggcgg cggtcgggt tgtttctggc ggaggtgctg ctgatgatgt aattaaagta   10980
ggcggtcttg agacggcgga tggtcgacag aagcaccatg tccttgggtc cggcctgctg   11040
aatgcgcagg cggtcggcca tgccccaggc ttcgttttga catcggcgca ggtctttgta   11100
gtagtcttgc atgagccttt ctaccggcac ttcttcttct ccttcctctt gtcctgcatc   11160
tcttgcatct atcgctgcgg cggcggcgga gtttggccgt aggtggcgcc ctcttcctcc   11220
catgcgtgtg accccgaagc ccctcatcgg ctgaagcagg gctaggtcgg cgacaacgcg   11280
ctcggctaat atggcctgct gcacctgcgt gagggtagac tggaagtcat ccatgtccac   11340
aaagcggtgg tatgcgcccg tgttgatggt gtaagtgcag ttggccataa cggaccagtt   11400
```

```
aacggtctgg tgacccggct gcgagagctc ggtgtacctg agacgcgagt aagccctcga    11460
gtcaaatacg tagtcgttgc aagtccgcac caggtactgg tatcccacca aaaagtgcgg    11520
cggcggctgg cggtagaggg gccagcgtag ggtggccggg gctccggggg cgagatcttc    11580
caacataagg cgatgatatc cgtagatgta cctggacatc caggtgatgc cggcggcggt    11640
ggtggaggcg cgcggaaagt cgcggacgcg gttccagatg ttgcgcagcg gcaaaaagtg    11700
ctccatggtc gggacgctct ggccggtcag gcgcgcgcaa tcgttgacgc tctaccgtgc    11760
aaaaggagag cctgtaagcg ggcactcttc cgtggtctgg tggataaatt cgcaagggta    11820
tcatggcgga cgaccggggt tcgagccccg tatccggccg tccgccgtga tccatgcggt    11880
taccgcccgc gtgtcgaacc caggtgtgcg acgtcagaca acgggggagt gctccttttg    11940
gcttccttcc aggcgcggcg gctgctgcgc tagcttttt ggccactggc cgcgcgcagc    12000
gtaagcggtt aggctggaaa cgaaagcat taagtggctc gctccctgta gccggagggt    12060
tattttccaa gggttgagtc gcgggacccc cggttcgagt ctcggaccgg ccggactgcg    12120
gcgaacgggg gtttgcctcc ccgtcatgca agaccccgct tgcaaattcc tccggaaaca    12180
gggacgagcc ccttttttgc ttttcccaga tgcatccggt gctgcggcag atgcgccccc    12240
ctcctcagca gcggcaagag caagagcagc ggcagacatg cagggcaccc tccctcctc    12300 ctaccgcgtc aggaggggcg acatccgcgg ttgacgcggc agcagatggt gattacgaac    12360
ccccgcggcg ccgggcccgg cactacctgg acttggagga gggcgagggc ctggcgcggc    12420
taggagcgcc ctctcctgag cggtacccaa gggtgcagct gaagcgtgat acgcgtgagg    12480
cgtacgtgcc gcggcagaac ctgtttcgcg accgcgaggg agaggagccc gaggagatgc    12540
gggatcgaaa gttccacgca gggcgcgagc tgcggcatgg cctgaatcgc gagcggttgc    12600
tgcgcgagga ggactttgag cccgacgcgc gaaccgggat tagtcccgcg cgcgcacacg    12660
tggcggccgc cgacctggta accgcatacg agcagacggt gaaccaggag attaactttc    12720
aaaaaagctt taacaaccac gtgcgtacgc ttgtggcgcg cgaggaggtg gctataggac    12780
tgatgcatct gtgggacttt gtaagcgcgc tggagcaaaa cccaaatagc aagccgctca    12840
tggcgcagct gttccttata gtgcagcaca gcagggacaa cgaggcattc agggatgcgc    12900
tgctaaacat agtagagccc gagggccgct ggctgctcga tttgataaac atcctgcaga    12960
gcatagtggt gcaggagcgc agcttgagcc tggctgacaa ggtggccgcc atcaactatt    13020
ccatgcttag cctgggcaag ttttacgccc gcaagatata ccatacccct tacgttccca    13080
tagacaagga ggtaaagatc gaggggttct acatgcgcat ggcgctgaag gtgcttacct    13140
tgagcgacga cctgggcgtt tatcgcaacg agcgcatcca caaggccgtg agcgtgagcc    13200
ggcggcgcga gctcagcgac cgcgagctga tgcacagcct gcaaagggcc ctggctggca    13260
cgggcagcgg cgatagagag gccgagtcct actttgacgc gggcgctgac ctgcgctggg    13320
ccccaagccg acgcgccctg gaggcagctg gggccggacc tgggctggcg gtggcacccg    13380
cgcgcgctgg caacgtcggc ggcgtggagg aatatgacga ggacgatgag tacgagccag    13440
aggacggcga gtactaagcg gtgatgtttc tgatcagatg atgcaagacg caacggaccc    13500
ggcggtgcgg gcggcgctgc agagccagcc gtccggcctt aactccacgg acgactggcg    13560
ccaggtcatg gaccgcatca tgtcgctgac tgcgcgcaat cctgacgcgt tccggcagca    13620
gccgcaggcc aaccggctct ccgcaattct ggaagcggtg gtcccggcgc gcgcaaaccc    13680
cacgcacgag aaggtgctgg cgatcgtaaa cgcgctggcc gaaaacaggg ccatccggcc    13740
```

```
cgacgaggcc ggcctggtct acgacgcgct gcttcagcgc gtggctcgtt acaacagcgg    13800
caacgtgcag accaacctgg accggctggt ggggatgtg cgcgaggccg tggcgcagcg     13860
tgagcgcgcg cagcagcagg gcaacctggg ctccatggtt gcactaaacg ccttcctgag    13920
tacacagccc gccaacgtgc cgcggggaca ggaggactac accaactttg tgagcgcact    13980
gcggctaatg gtgactgaga caccgcaaag tgaggtgtac cagtctgggc cagactattt    14040
tttccagacc agtagacaag gcctgcagac cgtaaacctg agccaggctt tcaaaaactt    14100 gcagggctg tgggggtgc gggctccac aggcgaccgc gcgaccgtgt ctagcttgct       14160
gacgcccaac tcgcgcctgt tgctgctgct aatagcgccc ttcacggaca gtggcagcgt    14220
gtcccgggac acatacctag gtcacttgct gacactgtac cgcgaggcca taggtcaggc    14280
gcatgtggac gagcatactt tccaggagat tacaagtgtc agccgcgcgc tgggcagga    14340 ggacacgggc agcctggagg caaccctaaa ctacctgctg accaaccggc ggcagaagat    14400
cccctcgttg cacagtttaa acagcgagga ggagcgcatt ttgcgctacg tgcagcagag    14460
cgtgagcctt aacctgatgc gcgacggggt aacgcccagc gtggcgctgg acatgaccgc    14520
gcgcaacatg gaaccgggca tgtatgcctc aaaccggccg tttatcaacc gcctaatgga    14580
ctacttgcat cgcgcggccg ccgtgaaccc cgagtatttc accaatgcca tcttgaaccc    14640
gcactggcta ccgccccctg gtttctacac cggggattc gaggtgcccg agggtaacga    14700
tggattcctc tgggacgaca tagacgacag cgtgttttcc ccgcaaccgc agaccctgct    14760
agagttgcaa cagcgcgagc aggcagaggc ggcgctgcga aaggaaagct ccgcaggcc    14820 aagcagcttg tccgatctag gcgctgcggc cccgcggtca gatgctagta gcccatttcc    14880
aagcttgata gggtctctta ccagcactcg caccacccgc ccgcgcctgc tgggcgagga    14940
ggagtaccta aacaactcgc tgctgcagcc gcagcgcgaa aaaaacctgc ctccggcatt    15000
tcccaacaac gggatagaga gcctagtgga caagatgagt agatggaaga cgtacgcgca    15060
ggagcacagg gacgtgccag gcccgcgccc gcccacccgt cgtcaaaggc acgaccgtca    15120
gcggggtctg gtgtgggagg acgatgactc ggcagacgac agcagcgtcc tggatttggg    15180
agggagtggc aacccgtttg cgcaccttcg ccccaggctg ggagaatgt tttaaaaaaa     15240 aaaaagcatg atgcaaaata aaaaactcac caaggccatg gcaccgagcg ttggttttct    15300
tgtattcccc ttagtatgcg gcgcgcggcg atgtatgagg aaggtcctcc tcctcctac    15360 gagagtgtgg tgagcgcggc gccagtggcg gcggcgctgg gttctcctt cgatgctccc     15420 ctggacccgc cgtttgtgcc tccgcggtac ctgcggccta ccgggggag aaacagcatc    15480 cgttactctg agttggcacc cctattcgac accaccgtg tgtacctggt ggacaacaag    15540
tcaacggatg tggcatccct gaactaccag aacgaccaca gcaactttct gaccacggtc    15600
attcaaaaca atgactacag cccgggggag gcaagcacac agaccatcaa tcttgacgac    15660
cggtcgcact gggcggcga cctgaaaacc atcctgcata ccaacatgcc aaatgtgaac    15720
gagttcatgt ttaccaataa gtttaaggcg cgggtgatgg tgtcgcgctt gcctactaag    15780
gacaatcagg tggagctgaa atacgagtgg gtggagttca cgctgcccga gggcaactac    15840
tccgagacca tgaccataga ccttatgaac aacgcgatct ggagcactac ttgaaagtg    15900 ggcagacaga acggggttct ggaaagcgac atcgggtaa agtttgacac ccgcaacttc    15960 agactgggt ttgaccccgt cactggtctt gtcatgcctg ggtatatac aaacgaagcc     16020 ttccatccag acatcatttt gctgccagga tgcggggtgg acttcaccca cagccgcctg    16080
agcaacttgt tgggcatccg caagcggcaa cccttccagg agggctttag gatcacctac    16140
```

```
gatgatctgg agggtggtaa cattcccgca ctgttggatg tggacgccta ccaggcgagc   16200
ttgaaagatg acaccgaaca gggcggggt ggcgcaggcg gcagcaacag cagtggcagc    16260
ggcgcggaag agaactccaa cgcggcagcc gcggcaatgc agccggtgga ggacatgaac   16320
gatcatgcca ttcgcggcga cacctttgcc acacgggctg aggagaagcg cgctgaggcc   16380
gaagcagcgg ccgaagctgc cgccccgct gcgcaacccg aggtcgagaa gcctcagaag    16440
aaaccggtga tcaaacccct gacagaggac agcaagaaac gcagttacaa cctaataagc   16500
aatgacagca ccttcaccca gtaccgcagc tggtaccttg catacaacta cggcgaccct   16560
cagaccggaa tccgctcatg gaccctgctt tgcactcctg acgtaacctg cggctcggag   16620
caggtctact ggtcgttgcc agacatgatg caagaccccg tgaccttccg ctccacgcgc   16680
cagatcagca actttccggt ggtgggcgcc gagctgttgc ccgtgcactc caagagcttc   16740
tacaacgacc aggccgtcta ctcccaactc atccgccagt ttacctctct gacccacgtg   16800
ttcaatcgct ttcccgagaa ccagattttg gcgcgcccgc cagcccccac catcaccacc   16860
gtcagtgaaa acgttcctgc tctcacagat cacgggacgc taccgctgcg caacagcatc   16920
ggaggagtcc agcgagtgac cattactgac gccagacgcc gcacctgccc ctacgtttac   16980
aaggccctgg gcatagtctc gccgcgcgtc ctatcgagcc gcactttttg agcaagcatg   17040
tccatcctta tatcgcccag caataacaca ggctggggcc tgcgcttccc aagcaagatg   17100
tttggcgggg ccaagaagcg ctccgaccaa cacccagtgc gcgtgcgcgg gcactaccgc   17160
gcgccctggg gcgcgcacaa acgcggccgc actgggcgca ccaccgtcga tgacgccatc   17220
gacgcggtgg tggaggaggc gcgcaactac acgcccacgc cgccaccagt gtccacagtg   17280
gacgcggcca ttcagaccgt ggtgcgcgga gcccggcgct atgctaaaat gaagagacgg   17340
cggaggcgcg tagcacgtcg ccaccgccgc cgacccggca ctgccgccca acgcgcggcg   17400
gcggccctgc ttaaccgcgc acgtcgcacc ggccgacggg cggccatgcg ggccgctcga   17460
aggctggccg cgggtattgt cactgtgccc cccaggtcca ggcgacgagc ggccgccgca   17520
gcagccgcgg ccattagtgc tatgactcag ggtcgcaggg gcaacgtgta ttgggtgcgc   17580
gactcggtta gcggcctgcg cgtgcccgtg cgcacccgcc ccccgcgcaa ctagattgca   17640
agaaaaaact acttagactc gtactgttgt atgtatccag cggcggcggc gcgcaacgaa   17700
gctatgtcca agcgcaaaat caagaagag atgctccagg tcatcgcgcc ggagatctat    17760 ggcccccga agaaggaaga gcaggattac aagccccgaa agctaaagcg ggtcaaaaag    17820
aaaaagaaag atgatgatga tgaacttgac gacgaggtgg aactgctgca cgctaccgcg   17880
cccaggcgac gggtacagtg gaaaggtcga cgcgtaaaac gtgttttgcg acccggcacc   17940
accgtagtct ttacgcccgg tgagcgctcc accgcacct acaagcgcgt gtatgatgag    18000
gtgtacggcg acgaggacct gcttgagcag gccaacgagc gcctcgggga gtttgcctac   18060
ggaaagcggg ataaggacat gctggcgttg ccgctggacg agggcaaccc aacacctagc   18120
ctaaagcccg taacactgca gcaggtgctg cccgcgcttg caccgtccga agaaaagcgc   18180
ggcctaaagc gcgagtctgg tgacttggca cccaccgtgc agctgatggt acccaagcgc   18240
cagcgactgg aagatgtctt ggaaaaaatg accgtggaac ctgggctgga gcccgaggtc   18300
cgcgtgcggc caatcaagca ggtggcgccg gactgggcg tgcagaccgt ggacgttcag    18360
atacccacta ccagtagcac cagtattgcc accgccacag agggcatgga gacacaaacg   18420
tccccggttg cctcagcggt ggcggatgcc gcggtgcagg cggtcgctgc ggccgcgtcc   18480
```

-continued

```
aagacctcta cggaggtgca aacggacccg tggatgtttc gcgtttcagc ccccggcgc    18540 ccgcgcggtt cgaggaagta cggcgccgcc agcgcgctac tgcccgaata tgccctacat    18600
ccttccattg cgcctacccc cggctatcgt ggctacacct accgcccag aagacgagca     18660 actacccgac gccgaaccac cactggaacc cgccgccgcc gtcgccgtcg ccagcccgtg    18720
ctggccccga tttccgtgcg cagggtggct cgcgaaggag gcaggaccct ggtgctgcca    18780
acagcgcgct accaccccag catcgtttaa aagccggtct ttgtggttct tgcagatatg    18840
gccctcacct gccgcctccg tttccggtg ccgggattcc gaggaagaat gcaccgtagg     18900
aggggcatgg ccggccacgg cctgacgggc ggcatgcgtc gtgcgcacca ccggcggcgg    18960
cgcgcgtcgc accgtcgcat gcgcggcggt atcctgcccc tccttattcc actgatcgcc    19020
gcggcgattg gcgccgtgcc cggaattgca tccgtggcct tgcaggcgca gagacactga    19080
ttaaaaacaa gttgcatgtg gaaaaatcaa aataaaaagt ctggactctc acgctcgctt    19140
ggtcctgtaa ctattttgta gaatggaaga catcaacttt gcgtctctgg ccccgcgaca    19200
cggctcgcgc ccgttcatgg gaaactggca agatatcggc accagcaata tgagcggtgg    19260
cgccttcagc tggggctcgc tgtggagcgg cattaaaaat ttcggttcca ccgttaagaa    19320
ctatggcagc aaggcctgga acagcagcac aggccagatg ctgagggata gttgaaaga    19380 gcaaaatttc caacaaaagg tggtagatgg cctggcctct ggcattagcg gggtggtgga    19440
cctggccaac caggcagtgc aaaataagat taacagtaag cttgatcccc gccctcccgt    19500
agaggagcct ccaccggccg tggagacagt gtctccagag gggcgtggcg aaaagcgtcc    19560
gcgccccgac agggaagaaa ctctggtgac gcaaatagac gagcctccct cgtacgagga    19620
ggcactaaag caaggcctgc ccaccacccg tcccatcgcg cccatggcta ccggagtgct    19680
gggccagcac acacccgtaa cgctggacct gcctcccccc gccgacaccc agcagaaacc    19740
tgtgctgcca ggcccgaccg ccgttgttgt aacccgtcct agccgcgcgt ccctgcgccg    19800
cgccgccagc ggtccgcgat cgttgcggcc cgtagccagt ggcaactggc aaagcacact    19860
gaacagcatc gtgggtctgg gggtgcaatc cctgaagcgc cgacgatgct tctgaatagc    19920
taacgtgtcg tatgtgtgtc atgtatgcgt ccatgtcgcc gccagaggag ctgctgagcc    19980
gccgcgcgcc cgcttttcaa gatggctacc ccttcgatga tgccgcagtg gtcttacatg    20040
cacatctcgg gccaggacgc ctcggagtac ctgagccccg ggctggtgca gtttgccccgc   20100 gccaccgaga cgtacttcag cctgaataac aagtttagaa accccacggt ggcgcctacg    20160
cacgacgtga ccacagaccg gtcccagcgt ttgacgctgc ggttcatccc tgtggaccgt    20220
gaggatactg cgtactcgta caaggcgcgg ttcaccctag ctgtgggtga taaccgtgtg    20280
ctggacatgg cttccacgta cttgacatc cgcggcgtgc tggacagggg ccctactttt     20340
aagccctact ctggcactgc ctacaacgcc ctggctccca agggtgcccc aaatccttgc    20400
gaatgggatg aagctgctac tgctcttgaa ataaacctag aagaaggga cgatgacaac     20460 gaagacgaag tagacgagca agctgagcag caaaaaactc acgtatttgg gcaggcgcct    20520
tattctggta taaatattac aaaggagggt attcaaatag gtgtcgaagg tcaaacacct    20580
aaatatgccg ataaaacatt tcaacctgaa cctcaaatag gagaatctca gtggtacgaa    20640
actgaaatta atcatgcagc tgggagagtc cttaaaaaga ctaccccaat gaaaccatgt    20700
tacggttcat atgcaaaacc cacaaatgaa aatggagggc aaggcattct tgtaaagcaa    20760
caaaatggaa agctagaaag tcaagtggaa atgcaatttt tctcaactac tgaggcgacc    20820
gcaggcaatg gtgataactt gactcctaaa gtggtattgt acagtgaaga tgtagatata    20880
```

```
gaaacccag acactcatat ttcttacatg cccactatta aggaaggtaa ctcacgagaa  20940
ctaatgggcc aacaatctat gcccaacagg cctaattaca ttgcttttag ggacaatttt  21000
attggtctaa tgtattacaa cagcacgggt aatatgggtg ttctggcggg ccaagcatcg  21060
cagttgaatg ctgttgtaga tttgcaagac agaaacacag agctttcata ccagcttttg  21120
cttgattcca ttggtgatag aaccaggtac ttttctatgt ggaatcaggc tgttgacagc  21180
tatgatccag atgttagaat tattgaaaat catggaactg aagatgaact tccaaattac  21240
tgctttccac tgggaggtgt gattaataca gagactctta ccaaggtaaa acctaaaaca  21300
ggtcaggaaa atggatggga aaagatgct acagaatttt cagataaaaa tgaaataaga  21360
gttggaaata attttgccat ggaaatcaat ctaaatgcca acctgtggag aaatttcctg  21420
tactccaaca tagcgctgta tttgcccgac aagctaaagt acagtccttc caacgtaaaa  21480
atttctgata acccaaacac ctacgactac atgaacaagc gagtggtggc tcccgggtta  21540
gtggactgct acattaacct tggagcacgc tggtcccttg actatatgga caacgtcaac  21600
ccatttaacc accaccgcaa tgctggcctg cgctaccgct caatgttgct gggcaatggt  21660
cgctatgtgc ccttccacat ccaggtgcct cagaagttct ttgccattaa aaacctcctt  21720
ctcctgccgg gctcatacac ctacgagtgg aacttcagga aggatgttaa catggttctg  21780
cagagctccc taggaaatga cctaaggggtt gacggagcca gcattaagtt tgatagcatt  21840
tgcctttacg ccaccttctt ccccatggcc cacaacaccg cctccacgct tgaggccatg  21900
cttagaaacg acaccaacga ccagtccttt aacgactatc tctccgccgc caacatgctc  21960
taccctatac ccgccaacgc taccaacgtg cccatatcca tccctcccg caactgggcg  22020
gctttccgcg gctgggcctt cacgcgcctt aagactaagg aaaccccatc actgggctcg  22080
ggctacgacc cttattacac ctactctggc tctataccct acctagatgg aaccttttac  22140
ctcaaccaca ccttttaagaa ggtgccatt acctttgact cttctgtcag ctggcctggc  22200
aatgaccgcc tgcttacccc caacgagttt gaaattaagc gctcagttga cggggagggt  22260
tacaacgttg cccagtgtaa catgaccaaa gactggttcc tggtacaaat gctagctaac  22320
tacaacattg gctaccaggg cttctatatc ccagagagct acaaggaccg catgtactcc  22380
ttctttagaa acttccagcc catgagccgt caggtggtgg atgatactaa atacaaggac  22440
taccaacagg tgggcatcct acaccaacac aacaactctg gatttgttgg ctaccttgcc  22500
cccaccatgc gcgaaggaca ggcctaccct gctaacttcc cctatccgct tataggcaag  22560
accgcagttg acagcattac ccagaaaaag tttctttgcg atcgcaccct ttggcgcatc  22620
ccattctcca gtaactttat gtccatgggc gcactcacag acctgggcca aaaccttctc  22680
tacgccaact ccgccacgc gctagacatg acttttgagg tggatccat ggacgagccc  22740
acccttcttt atgttttgtt tgaagtcttt gacgtggtcc gtgtgcaccg ccgcaccgc  22800
ggcgtcatcg aaaccgtgta cctgcgcacg cccttctcgg ccggcaacgc cacaacataa  22860
agaagcaagc aacatcaaca acagctgccg ccatgggctc cagtgagcag gaactgaaag  22920
ccattgtcaa agatcttggt tgtgggccat attttttggg cacctatgac aagcgctttc  22980
caggctttgt ttctccacac aagctcgcct gcgccatagt caatacggcc ggtcgcgaga  23040
ctgggggcgt acactggatg gcctttgcct ggaacccgca ctcaaaaaca tgctacctct  23100
ttgagccctt tggctttttct gaccagcgac tcaagcaggt ttaccagttt gagtacgagt  23160
cactcctgcg ccgtagcgcc attgcttctt cccccgaccg ctgtataacg ctggaaaagt  23220
```

```
ccacccaaag cgtacagggg cccaactcgg ccgcctgtgg actattctgc tgcatgtttc    23280
tccacgcctt tgccaactgg ccccaaactc ccatggatca caaccccacc atgaacctta    23340
ttaccggggt acccaactcc atgctcaaca gtccccaggt acagcccacc ctgcgtcgca    23400
accaggaaca gctctacagc ttcctggagc gccactcgcc ctacttccgc agccacagtg    23460
cgcagattag gagcgccact tcttttttgtc acttgaaaaa catgtaaaaa taatgtacta    23520
gagacacttt caataaaggc aaatgctttt atttgtacac tctcgggtga ttatttaccc    23580
ccacccttgc cgtctgcgcc gtttaaaaat caaaggggtt ctgccgcgca tcgctatgcg    23640
ccactggcag ggacacgttg cgatactggt gtttagtgct ccacttaaac tcaggcacaa    23700
ccatccgcgg cagctcggtg aagttttcac tccacaggct gcgcaccatc accaacgcgt    23760
ttagcaggtc gggcgccgat atcttgaagt cgcagttggg gcctccgccc tgcgcgcgcg    23820
agttgcgata cacagggttg cagcactgga acactatcag cgccgggtgg tgcacgctgg    23880
ccagcacgct cttgtcggag atcagatccg cgtccaggtc ctccgcgttg ctcagggcga    23940
acggagtcaa ctttggtagc tgccttccca aaaaggcgc gtgcccaggc tttgagttgc    24000
actcgcaccg tagtggcatc aaaaggtgac cgtgcccggt ctgggcgtta ggatacagcg    24060
cctgcataaa agccttgatc tgcttaaaag ccacctgagc ctttgcgcct tcagagaaga    24120
acatgccgca agacttgccg gaaaactgat tggccggaca ggccgcgtcg tgcacgcagc    24180
accttgcgtc ggtgttggag atctgcacca catttcggcc ccaccggttc ttcacgatct    24240
tggccttgct agactgctcc ttcagcgcgc gctgcccgtt ttcgctcgtc acatccattt    24300
caatcacgtg ctccttattt atcataatgc ttccgtgtag acacttaagc tcgccttcga    24360
tctcagcgca gcggtgcagc cacaacgcgc agcccgtggg ctcgtgatgc ttgtaggtca    24420
cctctgcaaa cgactgcagg tacgcctgca ggaatcgccc catcatcgtc acaaaggtct    24480
tgttgctggt gaaggtcagc tgcaacccgc ggtgctcctc gttcagccag gtcttgcata    24540
cggccgccag agcttccact tggtcaggca gtagtttgaa gttcgccttt agatcgttat    24600
ccacgtggta cttgtccatc agcgcgcgcg cagcctccat gcccttctcc cacgcagaca    24660
cgatcggcac actcagcggg ttcatcaccg taatttcact ttccgcttcg ctgggctctt    24720
cctcttcctc ttgcgtccgc ataccacgcg ccactgggtc gtcttcattc agccgccgca    24780
ctgtgcgctt acctcctttg ccatgcttga ttagcaccgg tgggttgctg aaacccacca    24840
tttgtagcgc cacatcttct ctttcttcct cgctgtccac gattacctct ggtgatggcg    24900
ggcgctcggg cttgggagaa gggcgcttct ttttcttctt gggcgcaatg gccaaatccg    24960
ccgccgaggt cgatggccgc gggctgggtg tgcgcggcac cagcgcgtct tgtgatgagt    25020
cttcctcgtc ctcggactcg atacgccgcc tcatccgctt ttttggggc gcccggggag    25080 gcggcggcga cggggacggg gacgacacgt cctccatggt tgggggacgt cgcgccgcac    25140
cgcgtccgcg ctcggggggtg gtttcgcgct gctcctcttc ccgactggcc atttccttct    25200
cctataggca gaaaaagatc atggagtcag tcgagaagaa ggacagccta accgcccct    25260 ctgagttcgc caccaccgcc tccaccgatg ccgccaacgc gcctaccacc ttccccgtcg    25320
aggcaccccc gcttgaggag gaggaagtga ttatcgagca ggacccaggt tttgtaagcg    25380
aagacgacga ggaccgctca gtaccaacag aggataaaaa gcaagaccag gacaacgcag    25440
aggcaaacga ggaacaagtc gggcgggggg acgaaaggca tggcgactac ctagatgtgg    25500
gagacgacgt gctgttgaag catctgcagc gccagtgcgc cattatctgc gacgcgttgc    25560
aagagcgcag cgatgtgccc ctcgccatag cggatgtcag ccttgcctac gaacgccacc    25620
```

```
tattctcacc gcgcgtaccc cccaaacgcc aagaaaacgg cacatgcgag cccaacccgc   25680
gcctcaactt ctaccccgta tttgccgtgc cagaggtgct tgccacctat cacatctttt   25740
tccaaaactg caagataccc ctatcctgcc gtgccaaccg cagccgagcg acaagcagc    25800 tggccttgcg gcagggcgct gtcatacctg atatcgcctc gctcaacgaa gtgccaaaaa   25860
tctttgaggg tcttggacgc gacgagaagc gcgcggcaaa cgctctgcaa caggaaaaca   25920
gcgaaaatga aagtcactct ggagtgttgg tggaactcga gggtgacaac gcgcgcctag   25980
ccgtactaaa acgcagcatc gaggtcaccc actttgccta cccggcactt aacctacccc   26040
ccaaggtcat gagcacagtc atgagtgagc tgatcgtgcg ccgtgcgcag cccctggaga   26100
gggatgcaaa tttgcaagaa caaacagagg agggcctacc cgcagttggc gacgagcagc   26160
tagcgcgctg gcttcaaacg cgcgagcctg ccgacttgga ggagcgacgc aaactaatga   26220
tggccgcagt gctcgttacc gtggagcttg agtgcatgca gcggttcttt gctgacccgg   26280
agatgcagcg caagctagag gaaacattgc actacaccct tcgacagggc tacgtacgcc   26340
aggcctgcaa gatctccaac gtggagctct gcaacctggt ctcctacctt ggaattttgc   26400
acgaaaaccg ccttgggcaa aacgtgcttc attccacgct caaggcgag gcgcgccgcg    26460 actacgtccg cgactgcgtt tacttatttc tatgctacac ctggcagacg gccatgggcg   26520
tttggcagca gtgcttggag gagtgcaacc tcaaggagtc gcagaaactg ctaaagcaaa   26580
acttgaagga cctatggacg gccttcaacg agcgctccgt ggccgcgcac ctggcggaca   26640
tcattttccc cgaacgcctg cttaaaaccc tgcaacaggg tctgccagac ttcaccagtc   26700
aaagcatgtt gcagaacttt aggaaccttta tcctagagcg ctcaggaatc ttgcccgcca   26760
cctgctgtgc acttcctagc gactttgtgc ccattaagta ccgcgaatgc cctccgccgc   26820
tttggggcca ctgctacctt ctgcagctag ccaactacct tgcctaccac ctgacataa    26880 tggaagacgt gagcggtgac ggtctactgg agtgtcactg tcgctgcaac ctatgcaccc   26940
cgcaccgctc cctggtttgc aattcgcagc tgcttaacga aagtcaaatt atcggtacct   27000
ttgagctgca gggtccctcg cctgacgaaa agtccgcggc tccggggttg aaactcactc   27060
cggggctgtg gacgtcggct taccttcgca aatttgtacc tgaggactac cacgcccacg   27120
agattaggtt ctacgaagac caatcccgcc cgccaaatgc ggagcttacc gcctgcgtca   27180
ttacccaggg ccacattctt ggccaattgc aagccatcaa caaagcccgc caagagtttc   27240
tgctacgaaa gggacggggg gtttacttgg accccagtc cggcgaggag ctcaacccaa    27300
tccccccgcc gccgcagccc tatcagcagc agccgcgggc ccttgcttcc caggatggca   27360
cccaaaaaga agctgcagct gccgccgcca cccacggacg aggaggaata ctgggacagt   27420
caggcagagg aggttttgga cgaggaggag gaggacatga tggaagactg ggagagccta   27480
gacgaggaag cttccgaggt cgaagaggtg tcagacgaaa caccgtcacc ctcggtcgca   27540
ttcccctcgc cggcgcccca gaaatcggca accggttcca gcatggctac aacctccgct   27600
cctcaggcgc cgccggcact gcccgttcgc cgacccaacc gtagatggga caccactgga   27660
accagggccg gtaagtccaa gcagccgccg ccgttagccc aagagcaaca acagcgccaa   27720
ggctaccgct catggcgcgg gcacaagaac gccatagttg cttgcttgca agactgtggg   27780
ggcaacatct ccttcgcccg ccgctttctt ctctaccatc acggcgtggc cttccccgt    27840 aacatcctgc attactaccg tcatctctac agcccatact gcaccggcgg cagcggcagc   27900
ggcagcaaca gcagcggcca cacagaagca aggcgaccg gatagcaaga ctctgacaaa    27960
```

```
gcccaagaaa tccacagcgg cggcagcagc aggaggagga gcgctgcgtc tggcgcccaa   28020
cgaacccgta tcgacccgcg agcttagaaa caggattttt cccactctgt atgctatatt   28080
tcaacagagc aggggccaag aacaagagct gaaaataaaa aacaggtctc tgcgatccct   28140
cacccgcagc tgcctgtatc acaaaagcga agatcagctt cggcgcacgc tggaagacgc   28200
ggaggctctc ttcagtaaat actgcgcgct gactcttaag gactagtttc gcgccctttc   28260
tcaaatttaa gcgcgaaaac tacgtcatct ccagcggcca cacccggcgc cagcacctgt   28320
cgtcagcgcc attatgagca aggaaattcc cacgccctac atgtggagtt accagccaca   28380
aatgggactt gcggctggag ctgcccaaga ctactcaacc cgaataaact acatgagcgc   28440
gggaccccac atgatatccc gggtcaacgg aatccgcgcc caccgaaacc gaattctctt   28500
ggaacaggcg gctattacca ccacacctcg taataacctt aatccccgta gttggcccgc   28560
tgccctggtg taccaggaaa gtcccgctcc caccactgtg gtacttccca gagacgccca   28620
ggccgaagtt cagatgacta actcagggc gcagcttgcg gcggctttc gtcacagggt   28680 gcggtcgccc gggcagggta taactcacct gacaatcaga gggcgaggta ttcagctcaa   28740
cgacgagtcg gtgagctcct cgcttggtct ccgtccggac gggacatttc agatcggcgg   28800
cgccggccgt ccttcattca cgcctcgtca ggcaatccta actctgcaga cctcgtcctc   28860
tgagccgcgc tctggaggca ttggaactct gcaatttatt gaggagtttg tgccatcggt   28920
ctactttaac ccccttctcgg gacctcccgg ccactatccg gatcaattta ttcctaactt   28980
tgacgcggta aaggactcgg cggacggcta cgactgaatg ttaagtggag aggcagagca   29040
actgcgcctg aaacacctgg tccactgtcg ccgccacaag tgctttgccc gcgactccgg   29100
tgagttttgc tactttgaat tgcccgagga tcatatcgag ggcccggcgc acggcgtccg   29160
gcttaccgcc cagggagagc ttgccgtag cctgattcgg gagtttaccc agcgcccct   29220 gctagttgag cgggacaggg gaccctgtgt tctcactgtg atttgcaact gtcctaacct   29280
tggattacat caagatcctc tagttaatta actagagtac ccggggatct tattcccttt   29340
aactaataaa aaaaataat aaagcatcac ttacttaaaa tcagttagca aatttctgtc   29400
cagtttattc agcagcacct ccttgccctc ctcccagctc tggtattgca gcttcctcct   29460
ggctgcaaac tttctccaca atctaaatgg aatgtcagtt tcctcctgtt cctgtccatc   29520
cgcacccact atcttcatgt tgttgcagat gaagcgcgca agaccgtctg aagatacctt   29580
caaccccgtg tatccatatg acacggaaac cggtcctcca actgtgcctt tcttactcc   29640 tcccttgta tccccaatg ggtttcaaga gagtccccct ggggtactct ctttgcgcct   29700
atccgaacct ctagttacct ccaatggcat gcttgcgctc aaaatgggca acggcctctc   29760
tctggacgag gccggcaacc ttacctccca aaatgtaacc actgtgagcc cacctctcaa   29820
aaaaaccaag tcaaacataa acctggaaat atctgcaccc ctcacagtta cctcagaagc   29880
cctaactgtg gctgccgccg cacctctaat ggtcgcgggc aacacactca ccatgcaatc   29940
acaggccccg ctaaccgtgc acgactccaa acttagcatt gccacccaag gaccctcac   30000 agtgtcagaa ggaaagctag ccctgcaaac atcaggcccc ctcaccacca ccgatagcag   30060
tacccttact atcactgcct caccccctct aactactgcc actggtagct gggcattga   30120 cttgaaagag cccatttata cacaaaatgg aaaactagga ctaaagtacg ggctcctttt   30180
gcatgtaaca gacgacctaa acactttgac cgtagcaact ggtccaggtg tgactattaa   30240
taatacttcc ttgcaaacta aagttactgg agccttgggt tttgattcac aaggcaatat   30300
gcaacttaat gtagcaggag gactaaggat tgattctcaa aacagacgcc ttatacttga   30360
```

```
tgttagttat ccgtttgatg ctcaaaacca actaaatcta agactaggac agggccctct   30420
ttttataaac tcagcccaca acttggatat taactacaac aaaggccttt acttgtttac   30480
agcttcaaac aattccaaaa agcttgaggt taacctaagc actgccaagg ggttgatgtt   30540
tgacgctaca gccatagcca ttaatgcagg agatgggctt gaatttggtt cacctaatgc   30600
accaaacaca aatccctca aaacaaaaat tggccatggc ctagaatttg attcaaacaa    30660
ggctatggtt cctaaactag gaactggcct tagttttgac agcacaggtg ccattacagt   30720
aggaaacaaa aataatgata agctaacttt gtggaccaca ccagctccat ctcctaactg   30780
tagactaaat gcagagaaag atgctaaact cactttggtc ttaacaaaat gtggcagtca   30840
aatacttgct acagtttcag ttttggctgt taaaggcagt ttggctccaa tatctggaac   30900
agttcaaagt gctcatctta ttataagatt tgacgaaaat ggagtgctac taaacaattc   30960
cttcctggac ccagaatatt ggaactttag aaatggagat cttactgaag gcacagccta   31020
tacaaacgct gttggattta tgcctaacct atcagcttat ccaaaatctc acggtaaaac   31080
tgccaaaagt aacattgtca gtcaagttta cttaaacgga gacaaaacta aacctgtaac   31140
actaaccatt acactaaacg gtacacagga aacaggagac acaactccaa gtgcatactc   31200
tatgtcattt tcatgggact ggtctggcca caactacatt aatgaaatat ttgccacatc   31260
ctcttacact ttttcataca ttgcccaaga ataaagaatc gtttgtgtta tgtttcaacg   31320
tgtttatttt tcaattgcag aaaatttcaa gtcattttc attcagtagt atagccccac    31380
caccacatag cttatacaga tcaccgtacc ttaatcaaac tcacagaacc ctagtattca   31440
acctgccacc tccctcccaa cacacagagt acacagtcct ttctccccgg ctggccttaa   31500
aaagcatcat atcatgggta acagacatat tcttaggtgt tatattccac acggtttcct   31560
gtcgagccaa acgctcatca gtgatattaa taaactcccc gggcagctca cttaagttca   31620
tgtcgctgtc cagctgctga gccacaggct gctgtccaac ttgcggttgc ttaacgggcg   31680
gcgaaggaga agtccacgcc tacatggggg tagagtcata atcgtgcatc aggataggc    31740
ggtggtgctg cagcagcgcg cgaataaact gctgccgccg ccgctccgtc ctgcaggaat   31800
acaacatggc agtggtctcc tcagcgatga ttcgcaccgc ccgcagcata aggcgccttg   31860
tcctccgggc acagcagcgc accctgatct cacttaaatc agcacagtaa ctgcagcaca   31920
gcaccacaat attgttcaaa atcccacagt gcaaggcgct gtatccaaag ctcatggcgg   31980
ggaccacaga acccacgtgg ccatcatacc acaagcgcag gtagattaag tggcgacccc   32040
tcataaacac gctggacata aacattacct cttttggcat gttgtaattc accacctccc   32100
ggtaccatat aaacctctga ttaaacatgg cgccatccac caccatccta aaccagctgg   32160
ccaaaacctg cccgccggct atacactgca gggaaccggg actggaacaa tgacagtgga   32220
gagcccagga ctcgtaacca tggatcatca tgctcgtcat gatatcaatg ttggcacaac   32280
acaggcacac gtgcatacac ttcctcagga ttacaagctc ctcccgcgtt agaaccatat   32340
cccagggaac aacccattcc tgaatcagcg taaatcccac actgcaggga agacctcgca   32400
cgtaactcac gttgtgcatt gtcaaagtgt tacattcggg cagcagcgga tgatcctcca   32460
gtatggtagc gcgggtttct gtctcaaaag gaggtagacg atccctactg tacggagtgc   32520
gccgagacaa ccgagatcgt gttggtcgta gtgtcatgcc aaatggaacg ccggacgtag   32580
tcatatttcc tgaagcaaaa ccaggtgcgg gcgtgacaaa cagatctgcg tctccggtct   32640
cgccgcttag atcgctctgt gtagtagttg tagtatatcc actctctcaa agcatccagg   32700
```

```
cgcccctgg cttcgggttc tatgtaaact ccttcatgcg ccgctgccct gataacatcc    32760
accaccgcag aataagccac acccagccaa cctacacatt cgttctgcga gtcacacacg    32820
ggaggagcgg gaagagctgg aagaaccatg tttttttttt tattccaaaa gattatccaa    32880
aacctcaaaa tgaagatcta ttaagtgaac gcgctcccct ccggtggcgt ggtcaaactc    32940
tacagccaaa gaacagataa tggcatttgt aagatgttgc acaatggctt ccaaaaggca    33000
aacggccctc acgtccaagt ggacgtaaag gctaaaccct tcagggtgaa tctcctctat    33060
aaacattcca gcaccttcaa ccatgcccaa ataattctca tctcgccacc ttctcaatat    33120
atctctaagc aaatcccgaa tattaagtcc ggccattgta aaatctgct ccagagcgcc    33180 ctccaccttc agcctcaagc agcgaatcat gattgcaaaa attcaggttc ctcacagacc    33240
tgtataagat tcaaaagcgg aacattaaca aaaataccgc gatcccgtag gtcccttcgc    33300
agggccagct gaacataatc gtgcaggtct gcacggacca gcgcggccac ttccccgcca    33360
ggaaccttga caaagaacc cacactgatt atgacacgca tactcggagc tatgctaacc    33420
agcgtagccc cgatgtaagc tttgttgcat gggcggcgat ataaaatgca aggtgctgct    33480
caaaaaatca ggcaaagcct cgcgcaaaaa agaaagcaca tcgtagtcat gctcatgcag    33540
ataaaggcag gtaagctccg gaaccaccac agaaaaagac accatttttc tctcaaacat    33600
gtctgcgggt ttctgcataa acacaaaata aataacaaa aaaacattta aacattagaa    33660
gcctgtctta caacaggaaa acaacccctt ataagcataa gacggactac ggccatgccg    33720
gcgtgaccgt aaaaaaactg gtcaccgtga ttaaaaagca ccaccgacag ctcctcggtc    33780 atgtccgag tcataatgta agactcggta aacacatcag gttgattcat cggtcagtgc    33840 taaaagcga ccgaaatagc ccgggggaat acatacccgc aggcgtagag acaacattac    33900
agcccccata ggaggtataa caaaattaat aggagagaaa aacacataaa cacctgaaaa    33960 acctcctgc ctaggcaaaa tagcaccctc ccgctccaga caacataca gcgcttcaca    34020 gcggcagcct aacagtcagc cttaccagta aaaagaaaa cctattaaaa aaacaccact    34080
cgacacggca ccagctcaat cagtcacagt gtaaaaaagg gccaagtgca gagcgagtat    34140
atataggact aaaaaatgac gtaacggtta aagtccacaa aaaacaccca gaaaaccgca    34200
cgcgaaccta cgcccagaaa cgaaagccaa aaaacccaca acttcctcaa atcgtcactt    34260
ccgttttccc acgttacgta acttcccatt ttaagaaaac tacaattccc aacacataca    34320
agttactccg ccctaaaacc tacgtcaccc gccccgttcc cacgcccgc gccacgtcac    34380 aaactccacc ccctcattat catattggct tcaatccaaa ataaggtata ttattgatga    34440
t                                                                    34441
```

```
<210> SEQ ID NO 11
<211> LENGTH: 310
<212> TYPE: DNA
<213> ORGANISM: Artificial
<220> FEATURE:
<223> OTHER INFORMATION: SV40 PolyA tail sequence

<400> SEQUENCE: 11
```

```
ggcctctggc cggagctgcc tggtcccaga gtggctgcac cacttccagg gtttattccc       60
tggtgccacc agccttccta tgggccccctt agcaatgtct taggaaagga gatcaacatt      120
ttcaaattag atgtttcaac tgtgctcctg ttttgtcttg aaagtggcac cagaggtgct      180
tctgcctgtg cagcgggtgc tgctggtaac agtggctgct tctctctctc tctctctctt      240
ttgggggctc attttgctg ttttgattcc cgggcttacc aggtgagaag tgaggaggga      300
```

```
                                          cgggatcccg                                                 310

<210> SEQ ID NO 12
<211> LENGTH: 1179
<212> TYPE: DNA
<213> ORGANISM: Artificial
<220> FEATURE:
<223> OTHER INFORMATION: LncRNA coding sequence

<400> SEQUENCE: 12
cctgcactgt cagcacttta gcagacaatg tagctaacaa tacactgcca tacttcttta     60
cattccaaat tcggttctac agggtcagtc tgataagcta tcacgattag cattatcagt    120
tctccgtcct gcactgtaag cactttagac tgtgagctcc tcgaaccact agtgacttca    180
ccgacagcaa tgaatgtctg cactgtcagc actttagcag acaatgtagc taacaataca    240
ctgccatact tctttacatt ccaaattcgg ttctacaggg tcagtctgat aagctatcac    300
gattagcatt atcagttctc cgtcctgcac tgtaagcact ttagactgtg agctcctcga    360
accactagtg acttcaccga cagcaatgaa tgtctgcact gtcagcactt tagcagacaa    420
tgtagctaac aatacactgc catacttctt tacattccaa attcggttct acagggtcag    480
tctgataagc tatcacgatt agcattatca gttctccgtc ctgcactgta agcactttag    540
actgtgagct cctcgaacca ctagtgactt caccgacagc aatgaatgtc tgcactgtca    600
gcactttagc agacaatgta gctaacaata cactgccata cttctttaca ttccaaattc    660
ggttctacag ggtcagtctg ataagctatc acgattagca ttatcagttc tccgtcctgc    720
actgtaagca ctttagactg tgagctcctc gaaccactag tgacttcacc gacagcaatg    780
aatgtctgca ctgtcagcac tttagcagac aatgtagcta acaatacact gccatacttc    840
tttacattcc aaattcggtt ctacagggtc agtctgataa gctatcacga ttagcattat    900
cagttctccg tcctgcactg taagcacttt agactgtgag ctcctcgaac cactagtgac    960
ttcaccgaca gcaatgaatg tctgcactgt cagcacttta gcagacaatg tagctaacaa   1020
tacactgcca tacttcttta cattccaaat tcggttctac agggtcagtc tgataagcta   1080
tcacgattag cattatcagt tctccgtcct gcactgtaag cactttagac tgtgagctcc   1140
tcgaaccact agtgacttca ccgacagcaa tgaatgtag                          1179

<210> SEQ ID NO 13
<211> LENGTH: 160
<212> TYPE: DNA
<213> ORGANISM: Artificial
<220> FEATURE:
<223> OTHER INFORMATION: LncRNA addition sequence

<400> SEQUENCE: 13
ttcgagcaac ttgtttattg cagcttataa tggttacaaa taaagcaata gcatcacaaa     60
tttcacaaat aaagcatttt tttcactgca ttctagttgt ggtttgtcca aactcatcaa    120
tgtatcttat catgtctgga tcgtctagca tcgaagatcc                          160

<210> SEQ ID NO 14
<211> LENGTH: 19
<212> TYPE: DNA
<213> ORGANISM: Artificial
<220> FEATURE:
<223> OTHER INFORMATION: primer

<400> SEQUENCE: 14
```
ctgcactgtc agcacttta                                               19

<210> SEQ ID NO 15
<211> LENGTH: 19
<212> TYPE: DNA
<213> ORGANISM: Artificial
<220> FEATURE:
<223> OTHER INFORMATION: primer

<400> SEQUENCE: 15
acattcattg ctgtcggtg                                               19

<210> SEQ ID NO 16
<211> LENGTH: 22
<212> TYPE: DNA
<213> ORGANISM: Artificial
<220> FEATURE:
<223> OTHER INFORMATION: primer

<400> SEQUENCE: 16
gatatactga gtcattaggg ac                                           22

<210> SEQ ID NO 17
<211> LENGTH: 22
<212> TYPE: DNA
<213> ORGANISM: Artificial
<220> FEATURE:
<223> OTHER INFORMATION: primer

<400> SEQUENCE: 17
ccaatagaat gagtgccaat at                                           22

<210> SEQ ID NO 18
<211> LENGTH: 21
<212> TYPE: DNA
<213> ORGANISM: Artificial
<220> FEATURE:
<223> OTHER INFORMATION: primer

<400> SEQUENCE: 18
atggcacaat ctcagctcac t                                            21

<210> SEQ ID NO 19
<211> LENGTH: 22
<212> TYPE: DNA
<213> ORGANISM: Artificial
<220> FEATURE:
<223> OTHER INFORMATION: primer

<400> SEQUENCE: 19
atcacggtga aaccttgtct ct                                           22

<210> SEQ ID NO 20
<211> LENGTH: 24
<212> TYPE: DNA
<213> ORGANISM: Artificial
<220> FEATURE:
<223> OTHER INFORMATION: primer

<400> SEQUENCE: 20
tatgtgttcg ctttgctata tgag                                         24

<210> SEQ ID NO 21
<211> LENGTH: 21
<212> TYPE: DNA
<213> ORGANISM: Artificial

-continued

```
<220> FEATURE:
<223> OTHER INFORMATION: primer

<400> SEQUENCE: 21
tcaggctcag gttcagacac a                                              21
```

LNCRNA AND ONCOLYTIC ADENOVIRUS, AND APPLICATION THEREOF

CROSS-REFERENCE TO RELATED APPLICATIONS

This application is a U.S. National Stage application under 35 U.S.C. § 371 of International Application PCT/CN2015/091892 (published as WO/2016/124002 A1), filed Oct. 14, 2015, which claims the benefit of priority to CN 201510056926.7 filed Feb. 4, 2015. Benefit of the filing date of each of these prior applications is hereby claimed. Each of these prior applications is hereby incorporated by reference in its entirety.

TECHNICAL FIELD

The present invention relates to the field of genetic engineering and virology. Specifically, it relates to an LncRNA competitively consuming OncomiRs and oncolytic adenovirus and application thereof.

BACKGROUND

Malignant tumor is a class of diseases, which is characterized by abnormal proliferation and metastasis of cells, and is a serious threat to people's health and lives. The morbidity and the mortality rates of malignant tumor have been on the rise in China. Currently, the treatment of malignant tumor is still focused on conventional surgery, radiotherapy and chemotherapy. For the vast majority of tumors, it is difficult to achieve the expected effect by the conventional treatment. No specific, sensitive early diagnostic index and the lack of effective therapeutic molecular target, which results in a little effect by the conventional treatment, have become an important obstacle to improve the clinical curative effect and prognosis in patients with tumor. Bioinformatics analysis has shown that one third of all human genes are regulated by microRNAs (miRNAs), which are small molecules that are large in number and widely distributed in cells and human body to play various functions, indicating that miRNAs are actually important components of gene regulation network. miRNAs play a key role in many biological processes, including the regulation of early cell development, cell proliferation, differentiation and apoptosis of stem cells. Attention has been paid to the regulation of miRNAs on the development of tumor and its important role in tumor diagnosis and treatment. Studies have shown that the abnormal expressed miRNAs in cancer cells are involved in origin, invasion and metastasis of tumor cells. Thus, the value of miRNAs for targeted tumor therapy is inestimable.

miRNAs, a length of 18-22 nucleotides, are small and highly conserved non-coding RNA molecules widely found in eukaryotic cells. First, miRNAs genes transfer into miRNAs transcribing precursors (pri-miRNAs) by RNA transcriptase in the cell nucleus. Then, pri-miRNAs are cut into miRNAs precursor (pre-miRNAs), a length of about 70 nucleotides, by RNA polymerase III. Finally, pre-miRNAs, transported from nucleus into cytoplasm, become single-stranded RNA molecules, a length of 18-22 nucleotides, by DICER enzyme. These single-stranded RNA molecules are mature miRNAs. miRNAs selectively and specifically bind with RNA-induced silencing complex (RISC) to form the RISC complex, which plays biological functions. miRNAs form an RNA-induced silencing complex (RISC) with other proteins and bind to the mRNAs of target genes through complementary nucleic acid sequences, resulting in degradation of target gene mRNAs or inhibition of its translation, which ultimately achieves post-transcriptional regulation of target genes. miRNAs are widely involved in many important progress in the organism lives, including individual development, organ formation, cell proliferation, cell differentiation, cell apoptosis, etc. In addition, miRNAs are participated in the development, invasion and metastasis of tumor. That the abnormal expression of miRNAs is closely related to a variety of malignant tumors has been proved by accumulating evidence. More than half of miRNAs are in tumor-related genomic regions or fragile sites, loss of heterozygosity section and expansion section, which shows that miRNAs may act as oncogenic miRNAs (OncomiRs) or tumor suppressor miRNAs to play their roles. In the development of tumor, miRNAs may change the expression of apoptosis-related factors, affect the activity of cell signaling pathways and regulate the activity of gene transcription factors. High expression of specific miRNAs has been found in different human tumor expression profiles of miRNAs, such as breast cancer, liver cancer, lung cancer, colorectal cancer, brain tumor, leukemia and so on. These miRNAs are regarded as a kind of OncomiRs. The up-regulation of miR-155 in chronic lymphocytic leukemia, Hodgkin's lymphoma, B-cell lymphoma, breast cancer, lung cancer, colon cancer or thyroid cancer, indicates that the disease in patients is difficult to be alleviated after treatment. The high expression of miR-17-92 family (miR-17-5p, miR-17-3p, miR-18a, miR-19a, miR-20a, miR-19b-1 and miR-92-1) is regarded as a maker for poor prognosis of multiple myeloma, and can promote malignant development of B-cell lymphoma. The expression of some miRNAs in tumor cells is down-regulated or even lost, resulting in the induction or promotion of tumor progression. This group of miRNAs can be considered as the tumor suppressor miRNAs. For example, the down-regulation of let-7 is related to tumorigenesis; miR-15 and miR-16 are related to chronic lymphocytic leukemia; the expression of miR-26a, miR-129, miR-143 and miR-145 in breast cancer, prostate cancer, cervical cancer, lymphatic system cancer and colorectal cancer is down-regulated; the down-regulated expression of miR-122 may mediate the pathogenesis of primary liver cancer. In a variety of tumors, miR-34, including miR-34a, miR-34b and miR-34c, etc, shows abnormal low expression. Changes in expression of miRNAs are closely related to tumorigenesis.

The miRNAs that are highly expressed in hepatocellular carcinoma (HCC) include miR-21, miR-221/222, miR-224, miR-17-5p/20a, miR-10b, miR-106b, miR-151-5p, miR-155, miR-181a/181b and miR-184. In addition, in HBV-related liver cancer, the miRNAs also include miR-1 and miR-449. According to the comparison of invasive and non-invasive miRNAs expression profiles of HCC, there are 20 miRNAs related to metastasis and postoperative recurrence of HCC. These miRNAs are divided into two parts, which are up-regulated expression and down-regulated expression, and they play different roles in the tumorigenesis respectively. miRNAs, which are up-regulated expression, include miR-185, miR-219-1, miR-207 and miR-338. miRNAs, which are down-regulated expression, include let-7g, miR-1-2, miR-122, miR-124a-2, miR-125b-2, miR-126, miR-148a, miR-148b, miR-15a, miR-194, miR-19a, miR-30a, miR-30c-1, miR-30e, miR-34a and miR-9-2. The overexpression of miR-21 in HCC can inhibit the expression of tumor-suppressor gene PTEN. PTEN is an important inhibitory protein of the phosphoinositide 3-kinase (PI3K)/serine threonine protein kinase (AKT) pathway. Therefore, the consequence of the inhibition of PTEN by miR-21 is the activation of the PI3K/AKT pathway, which promotes cancer cell proliferation and metastasis. miR-221/222 acts on many key tumor suppressors, including Bmf, $p27^{kip1}$, $p57^{kip216}$, PTEN, tissue inhibitors of metalloproteinases (TIMP-3), and DNA damage-inducible transcript 4 (DDIT4), to mediate the occurrence and progression of tumors. In a word, high expression of miR-21, miR-221/222, miR-224, miR-17-5p, miR-10b, miR106b, miR-151-5p, miR-155, miR-181a/181b or miR-184 can promote the proliferation, invasion and metastasis of HCC cells; high expression of miR-221/222, miR-224, miR-10b or miR-155 can inhibit HCC cell apoptosis; and high expression of miR-21, miR-221/222, miR-143, miR-1 or miR-449a can promote the replication of HBV, induce carcinogenesis and enhance cancer cell proliferation.

The difference in the miRNA expression profiles between tumor cells and normal tissue cells, as well as the specificity of the miRNA expression profiles between different tumors and the roles of miRNAs in tumorigenesis, metastasis and recurrence, have provided useful molecular targets for treatment of tumors by regulating miRNA expression. Recently, there have been many therapeutic strategies for tumors targeting miRNAs, which brings hope for treatment of tumors. With regard to over-expressed OncomiRs in tumor cells, studies have used miRNAs inhibitors or antisense sequences to block miRNA expression, thereby inhibiting tumor growth. However, most of the existing therapeutic studies focus on single miRNA or its family. The regulatory mechanisms of miRNAs are complex, one miRNA can regulate multiple target genes, and one target gene can be regulated by multiple miRNAs. Tumorigenesis and its progression involve many miRNAs, which regulate the expression of even more target genes or affect many signal transduction pathways. Therefore, the interference of single miRNA expression has a limited inhibitory effect on tumors, while cancer cells can easily regain their proliferation activity through alternative signal pathways.

The tumor-selective replicating adenovirus, the oncolytic adenovirus, can selectively replicate in large amounts in tumor cells and lyse tumor cells. The destroyed tumor cells release progeny viruses to continuously infect more tumor cells. Taking advantages of the selectively replicating ability in high copy numbers, the high dispersion ability and high transfection ability of the tumor-selective replicating adenovirus in tumor cells, the copy number of transgene carried by this type of virus will increase exponentially with the viral replication. The anti-cancer factor, with the high transfection, high copy number and high expression, could be got in tumor cells and improve anti-cancer ability of oncolytic adenovirus. Adenovirus, a common and secure virus vector in tumor gene therapy, has been widely used in human gene therapy. The advantages of adenovirus are as follows. The genomes of adenovirus are completely clear and easy to operate. Adenovirus can infect a variety of human cells and transduce different types of human tissue cells efficiently, including quiescent cells. Due to the high titer adenovirus, there are high titer recombinant virus products in cell cultures. Large exogenous genes can be introduced into the genome, because the genome of adenovirus is large. Although adenovirus can be into the cells, it is not integrated into the host cell genome. Thus, adenovirus is safe and non-carcinogenic. China Food and Drug Administration had approved 2 adenovirus products in 2004 and 2005, and significant side effects have been not found in clinical application.

Using the artificially-designed interfering LncRNA based on the tumor-selective replicating adenovirus to proliferate specifically in the tumor cell has not been reported yet. LncRNA, which is high copy and high efficient expression, can improve the effect of competitive binding with miRNAs, protect a variety of target genes of OncomiRs, and play a more effective anti-tumor effect eventually.

SUMMARY OF THE INVENTION

A primary object of the present invention is to provide an LncRNA, which competitively consumes OncomiRs in the treatment of tumors including liver cancer to achieve joint interference of multiple miRNAs, and to provide an oncolytic adenovirus, which can selectively proliferate in tumor cells and express the LncRNA.

Another object of the present invention is to provide an LncRNA, which competitively consumes OncomiRs, the LncRNA coding sequence is n copies of SEQ ID NO.4, and the n is an integer greater than or equal to 1.

As an embodiment of this invention, the n is equal to 6.

A further object of the present invention is to provide the LncRNA coding sequence, the LncRNA coding sequence is n copies of SEQ ID NO.1, and the n is an integer greater than or equal to 1.

As an embodiment of this invention, the n is equal to 6.

A still further object of the present invention is to provide an oncolytic adenovirus, the genome of which contains the expression cassette of the LncRNA.

As an embodiment of this invention, the expression cassette of the LncRNA contains the coding sequence of LncRNA and the promoter which can regulate the expression of the LncRNA coding sequence, the promoter, which can regulate the expression of the LncRNA coding sequence, is inserted before the transcriptional start sites of the LncRNA coding sequence.

As an embodiment of this invention, the genome of the oncolytic adenovirus contains the essential virus replication gene and the tumor-selective promoter, which can regulate the expression of the essential virus replication gene.

As an embodiment of this invention, the oncolytic adenovirus is based on human adenovirus type 5, the coding sequence of the promoter which can regulate the expression of the LncRNA coding sequence is SEQ ID NO.6, the coding sequence of the essential virus replication gene is SEQ ID NO.8, the coding sequence of the tumor-selective promoter is SEQ ID NO.7.

As an embodiment of this invention, the complete genome sequence of the oncolytic adenovirus is SEQ ID NO.10.

A still further object of the present invention is to provide the application of the LncRNA, the LncRNA coding sequence, and the oncolytic adenovirus in drug preparation, the drug is to be used in the treatment of tumor.

As an embodiment of this invention, the expression of miR-21, miR-221/222, miR-224, miR-17-5p, miR-10b, miR106b, miR-151-5p, miR-155, miR-181a/181b, miR-184, miR-1 and miR-449a in tumor is high.

As an embodiment of this invention, the tumor is liver cancer, particularly primary hepatocellular carcinoma.

A still further object of the present invention is to provide the application of the LncRNA, the LncRNA coding sequence, and the oncolytic adenovirus in reagent preparation, the reagent is to be used in the study of the molecular mechanism of liver cancer cells and the treatment of liver cancer.

The advantages of the present invention are to provide an LncRNA, which competitively consumes OncomiRs, an oncolytic adenovirus and application thereof. The significance is as follows:

The present invention has multiple effective anti-tumor mechanisms. Under effective regulation of the tumor selective Survivin gene promoter, the oncolytic adenovirus can selectively replicate in large amounts in tumor cells, lyse tumor cells, and release progeny viruses to continuously infect more tumor cells. The artificial-designed LncRNA, which can be expressed continuously in tumor cells, contains sequences which can complementarily bind with multiple OncomiRs. The artificial-designed LncRNA can bind with OncomiRs, competing with all of the target gene mRNAs of OncomiRs. And it can consume high-expressed OncomiRs, protect the tumor suppressor gene in cells, and play the role of anti-cancer. This treatment strategy can simultaneously and effectively block the functions of multiple OncomiRs that have different or complementary mechanisms. This treatment strategy also can inhibit multiple signal transduction pathways related to OncomiRs. The defects that the effect of single miRNA intervention on inhibiting tumor is limited and tumor cell can easily regain the proliferation activity through alternative signal pathways have been overcome. The expression of the artificial-designed LncRNA can be mediated by the tumor-selective replicating oncolytic adenovirus. The copy number and expression of LncRNA increase geometrically along with the selective replication of virus in tumor cells. The LncRNA, which has high copy numbers and high expression, can consume a lot of OncomiRs, protect the tumor suppressor gene in cells, inhibit tumorigenesis, and destroy tumor.

The present invention has multiple effective targeting security mechanisms. The Survivin promoter, as a cis-acting element, can be introduced between transcription beginning position of E1a, the essential gene of adenovirus replication, and the ATG translation initiation sites of it. This method can regulate the transcription of E1a, make E1a selectively express only in Suvivin-positive tumor cells, and has weak or no effect on normal cells. The regulation is more security and reliable. The artificial-designed LncRNA contains a set of sequences complementarily binding with OncomiRs which are highly expressed and promote tumorigenesis by various mechanisms. The aim is to consume or to interfere with OncomiRs, and is not active on other tumor-suppressive miRNAs. Normal cells are not affected because OncomiRs are not expressed or their expression level is extremely low in normal cells. Therefore, the anticancer therapeutic efficacy of this strategy is increased and the safety is improved. In addition, translation termination codon was introduced into the beginning and ending position of the LncRNA coding sequence, which can prevent LncRNA to be translated into protein or polypeptide.

The anti-cancer system of the LncRNA with adenovirus provided by the present invention can be used in the treatment for most types of malignant tumors, and it has not been reported at home and abroad. Based on the system, anti-tumor biological therapeutic products can be produced. Thus, this strategy has established a technology platform with a reliable therapeutic effect for the treatment of tumors.

FIGURE DESCRIPTION

FIG. 1 AdSVPE1a-lcnR replication in different cells at different time points.

Figure 2:
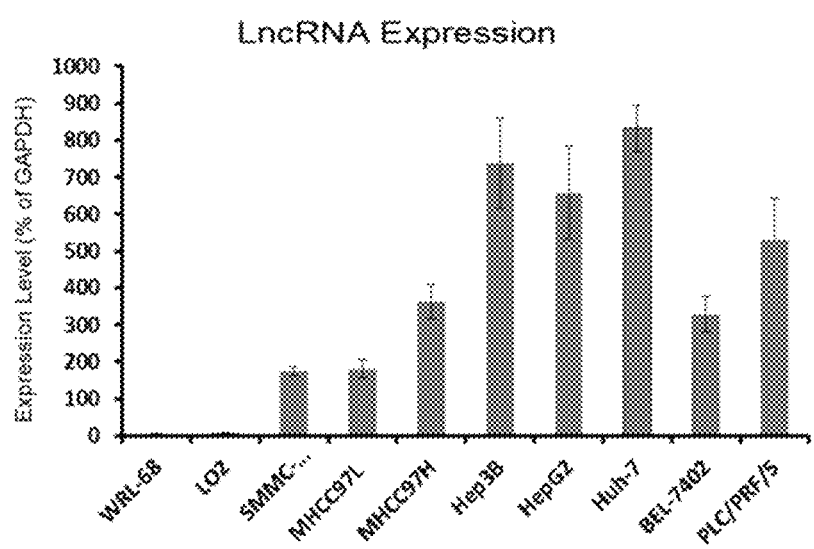

FIG. 2 AdSVPE1a-lcnR-midiated LncRNA expression at different cells.

Figure 3:
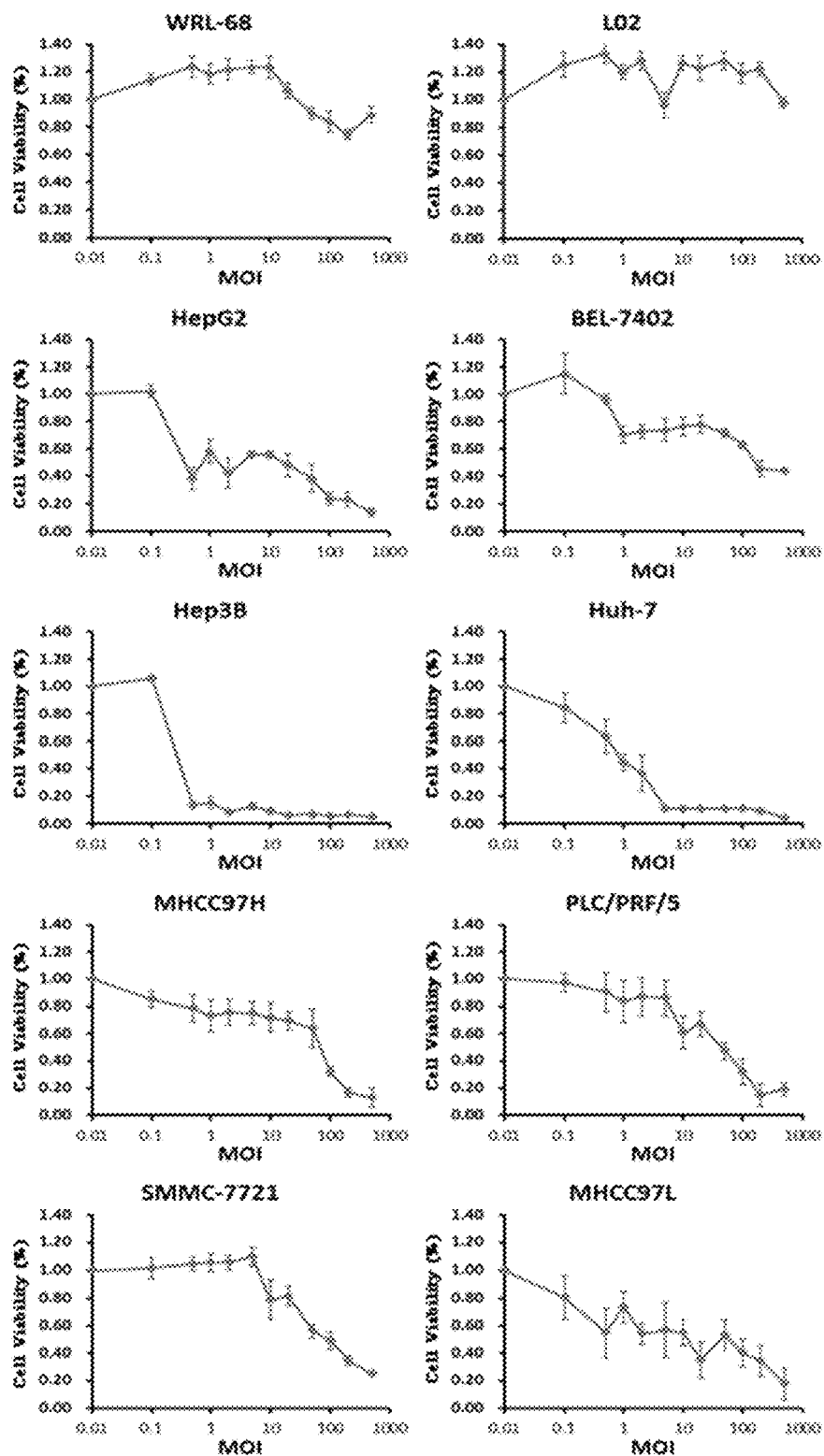

FIG. 3 The effect of AdSVPE1a-lcnR-midiated LncRNA expression on the cell viability.

Figure 4:
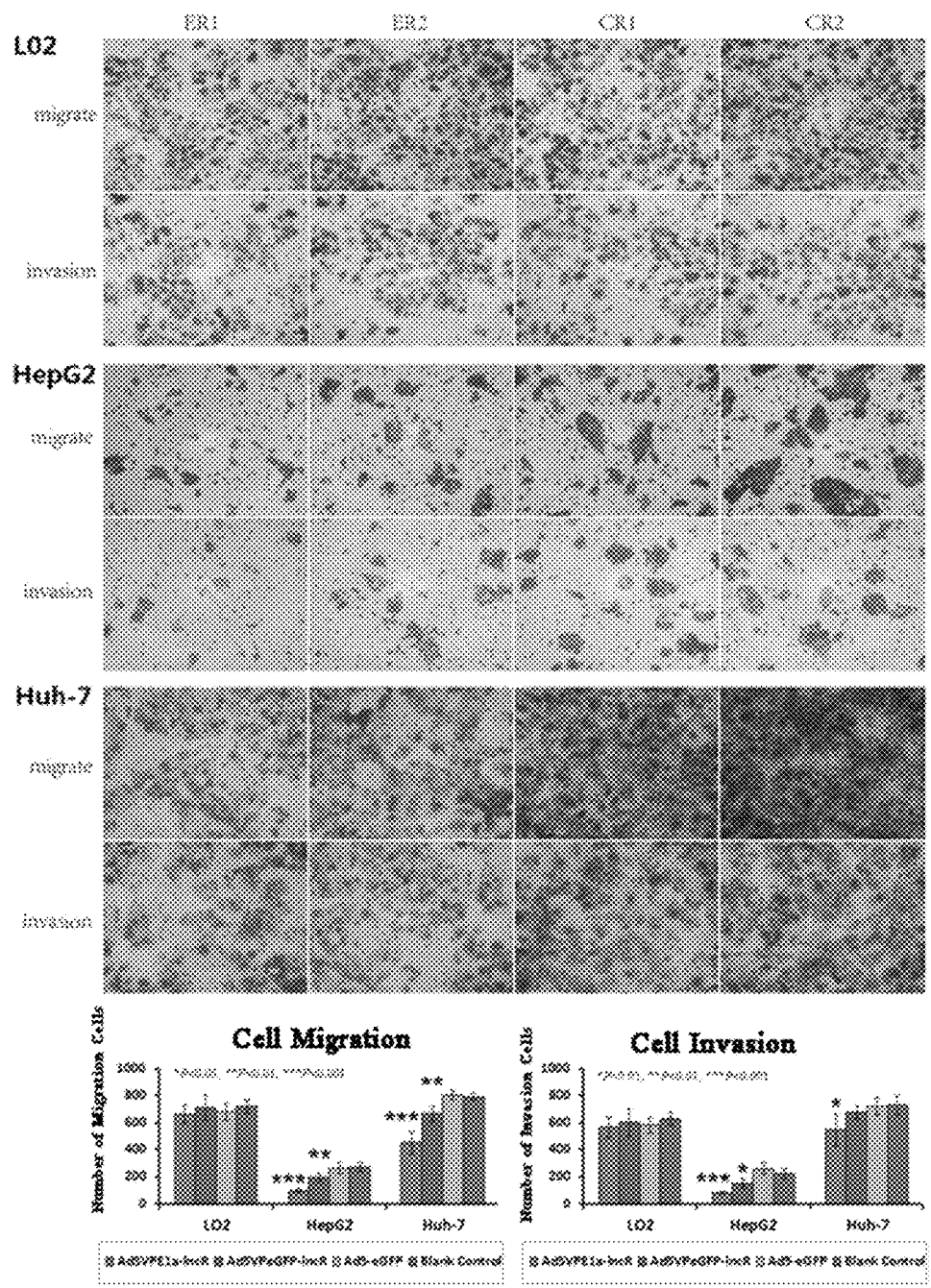

FIG. 4 The effect of AdSVPE1a-lcnR-midiated LncRNA expression on the cell migration and invasion.

Figure 5:
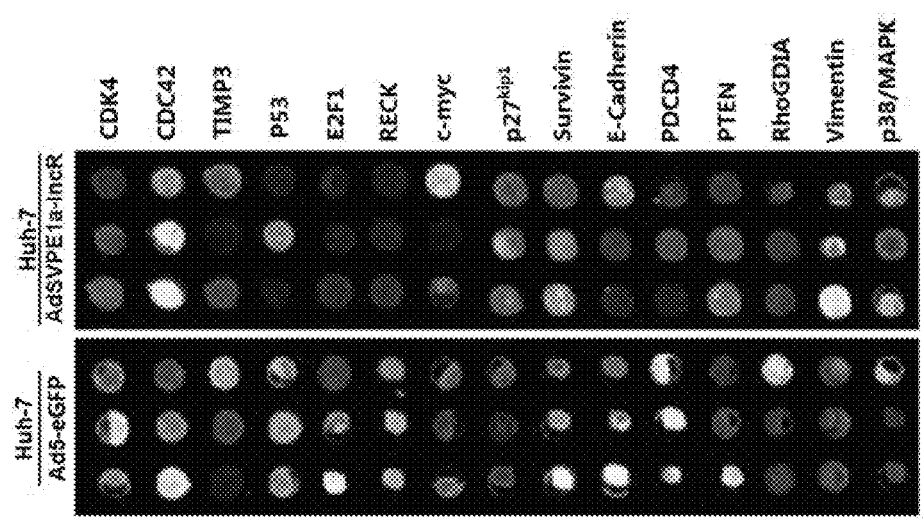

FIG. 5 The effect of AdSVPE1a-lcnR-midiated LncRNA expression on the expression profiles of HCC gene.

Figure 6:
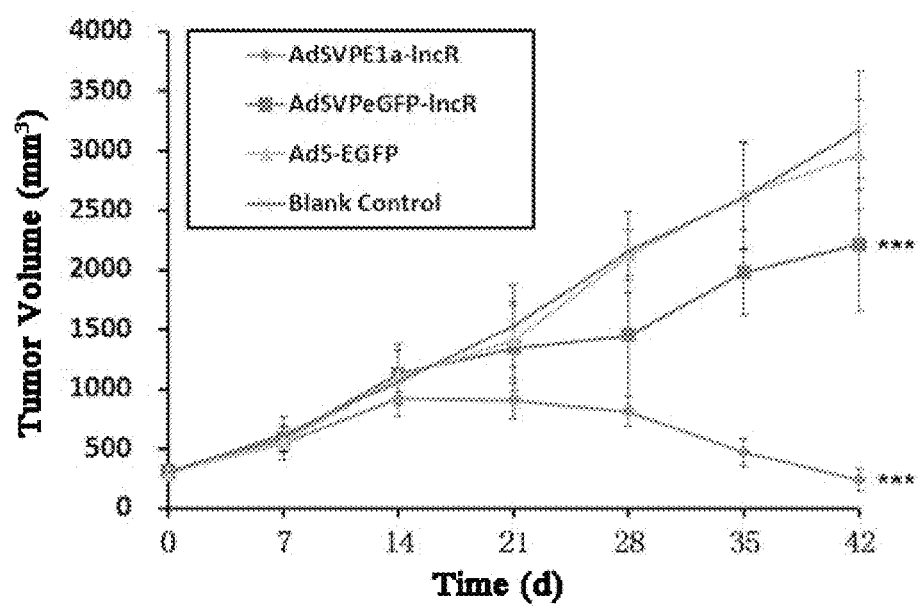

FIG. 6 AdSVPE1a-lcnR expression inhibits tumor growth of Huh-7 HCC cell xenografts in nude mice.

IMPLEMENTATION

The embodiments of the present invention are described in details with figures.

The inventors of the present application use tumor-selective Survivin promoter to regulate E1a, the essential gene of adenovirus replication, and make virus replicate selectively in tumor cells. The artificial-designed LncRNA coding sequence is expressed based on the oncolytic adenovirus, and contains a group of seed sequences which are complementary to OncomiRs sequences that promote the occurrence and progression of tumor cells. LncRNA can be highly expressed and copy in a large number by the selectively replication of adenovirus in tumor cells. LncRNA can bind with and consume OncomiRs by competing with OncomiRs target gene. Thus, the tumor suppressor gene can be protected from the interference and inhibition of OncomiRs. And the targeted intervention therapy for tumor can be achieved. The selectively replication of virus vector in tumor cells and the selectively interfere targeting OncomiRs assure, therefore, that the anticancer therapeutic efficacy of this strategy is increased and the safety is improved.

The LncRNA Coding Sequence

The LncRNA coding sequence is the DNA sequence that codes LncRNA. As an optimum embodiment of the present invention, the LncRNA coding sequence is SEQ ID NO.1. As a specific embodiment of the present invention, the LncRNA coding sequence is SEQ ID NO.2. In order to make the LncRNA coding sequence get strong transcription activity and not to be translated, CACCATGC is introduced into 5'-end and AG is introduced into 3'-end of SEQ ID NO.2. The introduced LncRNA coding sequence is SEQ ID NO.3. The aim of the introduced sequence is to add stop codon into the beginning and ending position of the LncRNA coding sequence. The stop codon can be TAG, TGA, or TAA.

The optimum LncRNA coding sequence of the present invention can be synthetic.

As a specific embodiment of the present invention, the LncRNA coding sequence contains a group of seed sequences which are complementary to OncomiRs sequences. The OncomiRs sequences can highly express and promote the occurrence and development of HCC cells by a variety of mechanisms. The OncomiRs sequences contain miR-21, miR-221/222, miR-224, miR-17-5p, miR-10b, miR-106b, miR-151-5p, miR-155, miR-181a/181b, miR-184, miR-1 and miR-449a. These sequences play different roles by acting on different target genes and signal pathways in the occurrence and development of HCC. For example, studies have found that high-expression of miR-21 in HCC can inhibit the expression of tumor-suppressor gene PTEN. PTEN is an important inhibitory protein of the phosphoinositide 3-kinase (PI3K)/serine threonine protein kinase (AKT) pathway. Therefore, the consequence of the inhibition of PTEN by miR-21 is the activation of the PI3K/AKT pathway, which promotes cancer cell proliferation and metastasis. miR-221/222 acts on many key tumor suppressors, including Bmf, $p27^{kip1}$, $p57^{kip216}$, PTEN, tissue inhibitors of metalloproteinases (TIMP-3), and DNA damage-inducible transcript 4 (DDIT4), to mediate the occurrence and progression of tumors. These miRNAs can be categorized according to their functions as follows: the high expression of miR-21, miR-221/222, miR-224, miR-17-5p, miR-10b, miR106b, miR-151-5p, miR-155, miR-181a/181b and miR-184 can promote the proliferation, invasion and metastasis of cancer cells; the high expression of miR-221/222, miR-224, miR-10b and miR-155 can inhibit cancer cell apoptosis; and the high expression of miR-21, miR-221/222, miR-143, miR-1 and miR-449a can promote the replication of HBV, induce carcinogenesis and enhance cancer cell proliferation. To inhibit the occurrence and development of HCC, the expression and function of these carcinogenic and tumor-promoting miRNAs should be inhibited by a variety of methods.

The present invention is not limited to the above examples. The LncRNA coding sequence can also contain a single or a group of sequences which are complementary to seed sequences of OncomiRs. The OncomiRs can be either a single or a group of OncomiRs in tumors cells other than HCC which can highly express and promote the occurrence and development of theses tumor cells by a variety of mechanisms, or a single or a group of OncomiRs in HCC cells except miR-21, miR-221/222, miR-224, miR-17-5p, miR-10b, miR-106b, miR-151-5p, miR-155, miR-181a/181b, miR-184, miR-1 and miR-449a.

LncRNA

LncRNA, long non-coding RNA, is a RNA molecule with a length between 200 and 100000 nt. LncRNA does not encode proteins, but regulates many progresses in cells.

LncRNA of the present invention can be encoded by the DNA sequence which contains a group of sequences complementary to seed sequences of OncomiRs that can promote the occurrence and development of HCC cells by a variety of mechanisms. As an optimum embodiment of the present invention, the encoded LncRNA sequence is SEQ ID NO.4. As a specific embodiment of the present invention, the copy number of the LncRNA coding sequence in the virus genome is 6. The encoded LncRNA sequence is SEQ ID NO.5. The effect of this LncRNA on competitively binding with OncomiRs is improved.

The Promoter of LncRNA Coding Sequence

The promoter of LncRNA coding sequence is used to start the transcription of LncRNA coding sequence. It contains other cis-acting elements that have the same function. The LncRNA coding sequence of the present invention in the virus genome can be regulated by any one of the following promoters or cis-acting elements including carcinoembryonic antigen promoter, AFP promoter, receptor tyrosine kinase (EGFR, Her-2, Her-3 and Her-4) promoter of human epidermal growth factor receptors (EGFRs), breast cancer associated antigen DF3/MUC1 promoter, vascular endothelial growth factor (VEGF) receptor KDR promoter, herpes simplexvirus promoter, E2F promoter, prostaglandin specific antigen promoter. As an optimum embodiment of the present invention, the LncRNA coding sequence is regulated by cytomegalovirus (CMV) promoter. This cis-acting element is introduced into the transcription beginning position of the LncRNA coding sequence, and can make sure that LncRNA is highly expressed in tumor cells infected by virus and exert biological activity. The sequence of CMV promoter is preferably as shown in SEQ ID NO.6.

Tumor-Selective Promoter

Tumor-selective promoter is a tumor-selective regulatory sequence. Many tumors have their own specific tumor markers. The expression of tumor markers is regulated by tumor-selective cis-acting or trans-acting elements. Thus, virus proliferation gene can be regulated by tumor-selective regulatory sequences, and virus can selectively proliferate in corresponding tissue cells but not in other tissue cells.

Tumor-selective promoter of the present invention can be composed by any one of the following promoters or enhancers, including (a) promoter, enhancer and mutant sequences of carcinoembryonic antigen, (b) promoter, enhancer and mutant sequences of AFP, (c) promoter, enhancer and mutant sequences of receptor tyrosine kinase of EGFRs, such as EGFR, Her-2, Her-3 and Her-4, (d) promoter, enhancer and mutant sequences of breast cancer associated antigen DF3/MUC1, (e) promoter, enhancer and mutant sequences of receptor KDR of VGEF, (f) promoter, enhancer and mutant sequences of L-plastin, (g) promoter, enhancer and mutant sequences of the members of inhibitor of apoptosis family of protein (IAP), (h) promoter, enhancer and mutant sequences of prostaglandin specific antigen, (i) hypoxic response element conserved sequences regulated by hypoxia inducible factor-1 (HIF-1), (j) promoter, enhancer and mutant sequences of transcription factor E2F.

Survivin, the apoptosis inhibitor, belongs to IAP. Survivin regulates the development of embryonic cell and cell cycle, inhibits apoptosis through a variety of ways and promotes cell proliferation and cell cycle progress. Survivin is only expressed in embryonic tissue and most tumor tissues, but not in normal adult tissues. The expression of Survivin in malignant tumors is highly selective. Survivin is expressed highly in most tumor tissues, such as lung cancer, colon cancer, pancreatic cancer, prostate cancer, breast cancer and non-Hodgkin's lymphoma. In addition, Survivin is related to the tumor recurrence and metastasis, as well as poor prognosis in patients. Thus, it becomes a broad spectrum of tumor diagnostic markers. In a word, virus that regulated by Survivin promoter is expected to achieve the broad spectrum of anti-cancer effect against most human tumors.

As an optimum embodiment of the present invention, the core sequence of Survivin promoter is introduced as cis-acting element between transcription beginning position and the ATG translation initiation sites of E1a, the essential gene of adenovirus replication. This method can regulate the transcription of E1a, make E1a be selectively expressed only in Suvivin-positive tumor cells, and have weak or no effect on normal cells. The regulation has more security and reliability. The sequence of Survivin promoter in this invention is SEQ ID NO.7.

The Essential Virus Replication Gene

The essential virus replication gene can provide the necessary proteins for virus replication. The essential adenovirus replication gene contains E1a, E1b-55 kDa, E1b-19 kDa, E3 and E4. E1b-55 kDa is the necessary protein for adenovirus replication in normal cells, but not in tumor cells. The selective deletion of E1b-55 kDa coding gene can keep the adenovirus replication in tumor cells but not in normal cells. E1b-55 kDa can inactivate and degrade P53 protein. The selective deletion of E1b-55 kDa coding gene has benefit in keeping the anti-tumor activity of P53 protein and improving the targeting of the virus vector. Adenovirus E1b-19 kDa coding gene is homologous to apoptosis-suppressing gene Bcl-2. E1b-19 kDa can bind with Bax or Bak and start the downstream apoptosis inhibitor procedure. In addition, E1b-19 kDa can destroy the apoptosis progress mediated by Fas to protect infected cells from killing effect mediated by TNF-α.

As an optimum embodiment of the present invention, the E1a sequence is SEQ ID NO.8.

Recombinant Oncolytic Adenovirus

The present invention uses recombinant virus vector to mediate the selective expression of the LncRNA coding sequence in tumor cells, which can exert anti-cancer effects. The recombinant virus vector contains existing virus vector, tumor-selective promoter and the expression cassette of the LncRNA. The expression cassette of the LncRNA contains the LncRNA coding sequence and the promoter of the LncRNA coding sequence.

Human oncolytic adenoviruses have six different subgenera, containing A, B, C, D, E and F. Their tropism, tumorigenesis and diseases history in host cells are different. As an optimum embodiment of the present invention, the oncolytic adenovirus is subgenus C type 5.

As an optimum embodiment of the present invention, the recombinant oncolytic adenovirus contains human adenovirus type 5, tumor-selective promoter and the expression cassette of the LncRNA. Using backbone plasmid pBH-GloxdeltaE1,3Cre which contains adenovirus type 5 genome and adenovirus shuttle plasmid which contains the LncRNA coding sequence to produce the recombinant oncolytic adenovirus by Cre-loxP recombinant enzyme cutting system in 293 cell. The sequence of outside the recombinant region in the recombinant oncolytic adenovirus is consistent with the sequence of outside the recombinant region in pBH-GloxdeltaE1,3Cre adenovirus vector. The sequence of inside the recombinant region in the recombinant oncolytic adenovirus is SEQ ID NO.9.

The SEQ ID NO.9 are as follows: 1-6 bp, XbaI restriction enzyme site; 7-996 bp, the sequence of Survivin promoter; 997-1002 bp, EcoRI restriction enzyme site; 1003-1991 bp, the cDNA sequence of E1a; 1992-2301 bp, SV40 PolyA tail sequence; 2302-2307 bp, BamHI restriction enzyme site; 2308-2338, the sequence of CMV promoter; 2339-2844 bp, SalI restriction enzyme site; 2845-2851, the LncRNA transcription beginning site; 2852-4030 bp, 6 duplicate copies of the LncRNA coding sequence; 4031-4190 bp, the LncRNA addition sequence; 4191-4196, SalI restriction enzyme site.

The whole genome sequence of the recombinant oncolytic adenovirus is SEQ ID NO.10. The whole genome sequence of the final recombinant oncolytic adenovirus subjects to SEQ ID NO.10 in the embodiment.

Embodiment.1 the Construction of Adenovirus Plasmid that Tumor-Selective Survivin Promoter Regulates E1a First step: The tumor-selective Survivin promoter was artificially synthesized. XbaI site was introduced in 5'-end, EcoRI site was introduced in 3'-end. To construct the plasmid pDC315-SVP that contains the Survivin promoter, the tumor-selective Survivin promoter was inserted between XbaI and EcoRI site of the plasmid pDC315 (PD-01-27, Microbix Biosysytems Inc., Canada). The length of the artificial-synthesis Survivin promoter was 1002 bp. The sequence of the artificial-synthesis Survivin promoter was based on SEQ ID NO.7, in which XbaI restriction enzyme site (TCTAGA) was introduced in 5'-end and EcoRI restriction enzyme site (GAATTC) was introduced in 3'-end.

Second step: The E1a sequence that contains PolyA tail sequence was attained by cloning. EcoRI site and ACC were introduced in 5'-end, BamHI site was introduced in 3'-end. To construct the plasmid pDC315-SVPE1a that the Survivin promoter regulates the expression of E1a, the E1a sequence was inserted between EcoRI and BamHI site of the plasmid pDC315-SVP. The length of E1a containing PolyA tail sequence was 1311 bp. In E1a, 1-6 bp, EcoRI restriction enzyme site (GAATTC); 7-9 bp, ACC; 10-995 bp, the cDNA sequence of E1a gene (SEQ ID NO.8); 996-1305 bp, SV40 PolyA tail sequence (SEQ ID NO.11); 1306-1311 bp, BamHI restriction enzyme site (GGATCC).

Embodiment.2 the Construction of Adenovirus Packaging Plasmid that Expresses the Artificial-Synthesis Long Non-Coding RNA (LncRNA)

First step: The CMV promoter sequence was attained by cloning. BamHI site was introduced in 5'-end, and SalI site was introduced in 3'-end. To construct the plasmid pDC315-mCMV that contains the mCMV promoter, the CMV promoter sequence was inserted between BamHI site and SalI site of the plasmid pDC315. The length of mCMV was 543 bp. In mCMV, 1-6 bp, BamHI restriction enzyme site (GGATCC); 7-537 bp, the CMV promoter sequence (SEQ ID NO.6); 538-543 bp, SalI restriction enzyme site (GTCGAC).

Second step: 6 copies of the DNA sequence encoding LncRNA that contains PolyA tail sequence were artificially synthesized. SalI site was introduced in 5'-end and 3'-end. To construct the expression plasmid pDC315-mCMVLncR that contains the LncRNA coding sequence, 6 copies of the DNA sequence encoding LncRNA was inserted between two SalI sites of the plasmid pDC315-mCMV. The length of the DNA sequence was 1348 bp. In the DNA sequence, 1-6 bp, SalI restriction enzyme site (GTCGAC); 7-13 bp, the transcription beginning site (CACCATG); 14-1192 bp, 6 duplicate copies of the LncRNA coding sequence (SEQ ID NO.12); 1193-1352 bp, the LncRNA addition sequence (SEQ ID NO.13); 1353-1358 bp, SalI restriction enzyme site (GTCGAC).

Third step: To construct the tumor-selective proliferation adenovirus packaging plasmid pDC315-SVPE1a-mCMV-LncR that contains the LncRNA coding sequence, the pDC315-mCMVLncR fragment that contains whole LncRNA expression cassette was recycled by restriction enzyme digestion of BamHI and SalI, and inserted between BamHI and SalI site of the plasmid pDC315-SVPE1a. The length of whole LncRNA expression cassette was 1895 bp. In whole LncRNA expression cassette, 1-6 bp, BamHI restriction enzyme site; 7-537 bp, the CMV promoter sequence (SEQ ID NO.6); 538-543 bp, SalI restriction enzyme site; 544-550 bp, the transcription beginning site (CACCATG); 551-1729 bp, 6 duplicate copies of the LncRNA coding sequence (SEQ ID NO.12); 1730-1889 bp, the LncRNA addition sequence (SEQ ID NO.13); 1890-1895 bp, SalI restriction enzyme site.

Embodiment.3 the Recombination, Amplification and Purification of Tumor-Selective Replication Adenovirus Containing the LncRNA Coding Sequence First step: The constructed type 5 adenovirus left arm packaging plasmid pDC315-SVPE1a-mCMVLncR and type 5 adenovirus right arm packaging plasmid pBHGloxdelE13cre (Microbix Biosysytems Inc., Canada) were cotransfected into HEK293 cells (Microbix Biosysytems Inc., Canada) by LipoFectamine2000. The cotransfection method was referred to Invitrogen's Lipo-Fectamine2000 kit operation instructions. The recombinant enzyme system Cre/Loxp of pBHGloxdelE13cre that contains type 5 adenovirus right arm and lacks of E1 and E3, can ensure efficient restructure of virus. HEK293 cells were transformed by sheared type 5 adenovirus DNA containing type5 adenovirus E1. Adenovirus DNA had high transfection efficiency on HEK293 cells, that can promote the recombination and packaging of adenovirus. 14 days after cotransfection, virus plaques appear. Adenovirus AdSVPE1a-LncR was restructured after 3 times virus plaque purification referring to the literature: GeneTransfer and Expression Protocols, Murray E J, Humana Press, Clifton, N.J.

The whole adenovirus AdSVPE1a-LncR gene sequence was SEQ ID NO.10. In the sequence, 1-85 bp, type 5 adenovirus ITR sequence; 86-437 bp, type 5 adenovirus gene sequence; 438-443 bp, XbaI restriction enzyme site; 444-1433 bp, the Survivin promoter sequence; 1434-1439 bp, EcoRI restriction enzyme site; 1440-2428 bp, the cDNA sequence of E1a gene; 2429-2738 bp, SV40 PolyA tail sequence; 2739-2744 bp, BamHI restriction enzyme site; 2745-3275 bp, the CMV promoter sequence; 3276-3281 bp, SalI restriction enzyme site; 3282-3288 bp, the LncRNA transcription beginning site; 3289-4467 bp, 6 duplicate copies of the LncRNA coding sequence; 4468-4627 bp, the LncRNA addition sequence; 4628-4633 bp, SalI restriction enzyme site; 4634-4668 bp, the LoxP sequence; 4669-34339 bp, type 5 adenovirus genome sequence; 34340-34441 bp, type 5 adenovirus ITR sequence.

Second step: The adenovirus AdSVPE1a-LncR replicated in a large number in HEK293 cells. The adenovirus was purified using the cesium chloride gradient centrifugation method referring to the literature: GeneTransfer and Expression Protocols, Murray E J, Humana Press, Clifton, N.J.
Embodiment.4 the Identification of Recombinant Adenovirus AdSVPE1a-LncR The inserted sequence of the recombinant adenovirus AdSVPE1a-LncR was identified by sequencing and PCR. AdSVPE1a-LncR was type 5 adenovirus. The inserted sequence contained 6 duplicate copies of the LncRNA coding sequence, mCMV promoter, Survivin promoter and E1a sequence. The other DNA sequence was the same with type 5 adenovirus. PCR primers for identification were listed in table. 1.

72 h. Cells were harvested, and the viral titer was detected with the TCID50 method. The specific replication ability of AdSVPE1a-LncR was strong in HepG2, Hep3B, MHCC97H, Huh-7 and PLC/PRF/5 cells, with the highest value reaching to 68465.66-fold (Huh-7). The specific replication ability reached to several hundred folds in SMMC-7721 and MHCC97L cells, whereas the replications in the normal cells, L02 and WRL-68, were not significant (FIG. 1).

Second step: The selective and high expression of LncRNA. The abovementioned cells were infected with the AdSVPE1a-LncR adenovirus (MOI=1 pfu/cell). After culture for 48 h, cells were harvested. The quantitative real-time PCR (qRT-PCR) was used to detect LncRNA expression. The following LncRNA-specific PCR primers were used: LncR-F (5'-CTGCACTGTC AGCACTTTA-3'); LncR-R (5'-ACATTCATT GCTGTCGGTG-3'). AdSVPE1a-LncR-mediated LncRNA expression levels were high in Huh-7, Hep3B, and HepG2 cells, followed by PLC/PRF/5, MHCC97H, BEL-7402, MHCC97L and SMMC-7721 cells. The LncRNA expression in the normal liver cells, WRL-68 and L02, was very low (FIG. 2).
Embodiment.6 the Effect of the Recombinant Adenovirus AdSVPE1a-LncR on the Biological Behavior of HCC Cells First step: The effect of LncRNA expression on the proliferation of cells. The effects of virus AdSVPE1a-LncR on HCC cells and normal cells were detected by the tetrazolium colorimetric assay (MTT assay). Cell Proliferation Kit I (MTT) was purchased from Roche Diagnostics GmbH. The cells in logarithmic growth phase were harvested and counted. The cells were diluted with 10% serum-containing

TABLE 1

PCR primers of identifying the recombinant adenovirus AdSVPE1a-LncR

| Primer sequence (5'-3') | SEQ ID NO. | Fragment length (BP) |
|---|---|---|
| LncR-F: CTGCACTGTCAGCACTTTA | 14 | 196, 392, 588, 784, 784, 980, 1176; copy number ratio is 7:6:5:4:3:2:1 |
| LncR-R: ACATTCATTGCTGTCGGTG | 15 | |
| mCMV-F: GATATACTGAGTCATTAGGGAC | 16 | 445 |
| mCMV-R: CCAATAGAATGAGTGCCAATAT | 17 | |
| SurvPro-F: ATGGCACAATCTCAGCTCACT | 18 | 149 |
| SurvPro-R: ATCACGGTGAAACCTTGTCTCT | 19 | |
| E1a-F: TATGTGTTCGCTTTGCTATATGAG | 20 | 188 |
| E1a-R: TCAGGCTCAGGTTCAGACACA | 21 | |

Results: The target bands with the same theoretical lengths were amplified by PCR using these primers sequence, and the sequences were correct by sequencing.
Embodiment.5 the Recombinant Adenovirus AdSVPE1a-LncR Proliferation and Gene Expression in HCC Cells First step: The selective proliferation experiment of the recombinant adenovirus AdSVPE1a-LncR. The HCC cells (HepG2, Hep3B, SMMC-7721, MHCC97H, MHCC97L, Huh-7 and PLC/PRF/5) and normal liver cells (L02 and WRL-68) were harvested, counted and seeded into 96-well plates (1×10$^4$ cells/well). After cell attachment, the medium was changed to serum-free medium. The AdSVPE1a-LncR virus was added at a multiplicity of infection (MOI) of 1 pfu/cell. 2 h after virus infection, cells were re-fed with medium containing 5% serum and cultured for 0, 24, 48 and culture medium, seeded in 96-well plates (1×10$^4$ cells/well in 100 μl). After cell attachment, virus was diluted with serum-free culture medium, and 100 μl of corresponding virus was added (MOI=1, 2, 5, 10, 20, 50 and 100 pfu/cell). For each MOI value, eight replicate wells were prepared. The cells were incubated for 2 h, and the cell culture medium was then changed to serum-containing medium (100 μl/well). After culture for 48 h, the medium was discarded, and 100 μl of 0.1 mol/L PBS was added to each well. The MTT labeling reagent (10 μl/well) was then added at a final concentration of 0.5 mg/ml, and the cells were incubated in an incubator for 4 h. Solubilization solution (10% SDS in 0.01 mol/L HCl) was then added (100 μl/well), and the plate was incubated overnight in an incubator. The absorbance at 570 nm wavelength was measured by Model 550 Microplate Reader (BIO-RAD), and the calibration wavelength was 655 nm. Then curve was drew. The experiments showed that AdSVPE1a-LncR had the strongest killing activity in Hep3B and Huh-7 cells. The viability of Hep3B cells was decreased to less than 50% when the adenovirus was added at an MOI of 0.5 pfu/cell and further decreased to less than 10% when the MOI was equal to 2 pfu/cell. The viability of Huh-7 cells was decreased to less than 50% when the MOI was equal to 1 pfu/cell and further decreased to less than 10% when the MOI was equal to 100 pfu/cell. AdSVPE1a-LncR had a stronger killing activity in HepG2 and MHCC97L cells, as their viabilities were all less than 50% when the virus was added at an MOI of 20 pfu/cell. AdSVPE1a-LncR had a stronger killing activity in PLC/PRF/5 cell, as its viability was less than 50% when the virus was added at an MOI of 50 pfu/cell. AdSVPE1a-LncR had a stronger killing activity in MHCC97H and SMMC-7721 cells, as their viabilities were all less than 50% when the virus was added at an MOI of 100 pfu/cell. AdSVPE1a-LncR had a weaker killing activity in BEL-7402 cells, as it decreased the viability to less than 50% at an MOI of 200 pfu/cell. AdSVPE1a-LncR did not have a significant impact on the proliferation of normal liver cells because the cell viability was greater than 80% when the MOI was equal to 500 pfu/cell.

Second step: The effect of LncRNA expression on cell migration and invasion ability. There were four experiment groups, including: the tumor cells infected by AdSVPE1a-LncR at a MOI of 10 pfu/cell (ER1), the tumor cells infected by AdSVPeGFP-LncR which was used as positive virus (ER2, non-proliferative virus that expressed LncRNA), the tumor cells infected by Ad5-eGFP which was used as negative virus (CR2, non-proliferative virus that did not express LncRNA), the parental cells cultured at the same time as a blank control (CR2). Cells were added to the top chamber of Transwell plate ($4\times10^5$ cells/200 µl). Medium containing 10% FBS (500 µl) was added to the bottom chamber. If cell invasion ability was monitored, Matrigel (polycarbonate membrane) was added to the top chamber. After culture for 24 h, the cells in the top chamber were removed and stained with 0.1% crystal violet for 20 min. Three fields (×200) were randomly imaged using the light microscope for counting. The experiment was repeated three times. The experiments showed that AdSVPE1a-LncR had a significant inhibitory effect on the cell migration and invasion ability of HCC cells. AdSVPeGFP-LncR also inhibited HCC cell migration and invasion, but its activity was significantly weaker than that of AdSVPE1a-LncR. AdSVPE1a-lncR and AdSVPeGFP-LncR did not significantly inhibit the mobility of normal liver cells (FIG. 4).

Embodiment.7 the Effect of the Recombinant Adenovirus AdSVPE1a-LncR on the HCC Cell Gene Expression Profile The Huh-7 cells in logarithmic growth phase were harvested and seeded in a 24-well plate ($1\times10^6$ cells/well in 100 µl). After cell attachment, the virus was diluted with serum-free medium, and 100 µl of AdSVPE1a-LncR was added (MOI=10 pfu/cell). The Ad5-eGFP was used as a negative virus control, while the parental cells were synchronously cultured as a blank control. Th cells were cultured in an incubator for 2 h and then re-fed with 100 µl/well of serum-containing medium. After culture for 48 h, the cells were harvested and total cellular protein was extracted for gene expression analysis using gene expression profile chip. The blank control was labeled with green fluorescence signal cy3, and the experiment group was labeled with red fluorescence signal cy5. Two fluorescence signal were superimposed. It was green when cy3 signal was stronger, and genes were down-regulated when the difference was less than 0.5 fold. It was red when cy5 signal was stronger, and genes were up-regulated when the difference was up to 2 fold. It was yellow when cy3 and cy5 signal was similar, and genes expression difference were between 0.5 and 2 fold. The expression profile of genes in Huh-7 infected with AdSVPE1a-LncR was significantly different. 708 genes were up-regulated, including, 13 proto-oncogenes and anti-oncogenes, 11 ion channel and transport protein relative genes, 12 cyclin relative genes, 13 cytoskeleton and movement protein relative genes, 5 apoptosis-related protein relative genes, 6 DNA-synthesis, -repair and -recombinant protein relative genes, 30 DNA-binding and -transcription factor relative genes, 10 cell receptor relative genes, 27 immune-related protein relative genes, 74 cell signal transduction protein relative genes, 61 metabolism molecular relative genes, 48 protein translation and synthesis factor relative genes, 9 differentiation and development relative genes, and 389 other relative genes. 628 genes were down-regulated, including 12 proto-oncogenes and anti-oncogenes, 14 ion channel and transport protein relative genes, 21 cyclin relative genes, 32 cytoskeleton and movement protein relative genes, 5 apoptosis-related protein relative genes, 7 DNA-synthesis, -repair and -recombinant protein relative genes, 17 DNA-binding and -transcription factor relative genes, 12 cell receptor relative genes, 31 immune-ralated protein relative genes, 59 cell signal transduction protein relative genes, 63 metabolism molecular relative genes, 48 protein translation and synthesis factor relative genes, 8 differentiation and development relative genes, and 299 other relative genes. The expression of PTEN, $p27^{ki1}$, TIMP3 and RECK was increased significantly, and the expression of p38/MAPK, Survivin, CDK4 and c-myc was decreased significantly (FIG. 5).

Embodiment.8 the Inhibitory Effect of the Recombinant Adenovirus AdSVPE1a-LncR on HCC Cell Line Xenograft Models in Nude Mice Forty healthy purebred five-week old male BALB/C nude mice were provided by Shanghai SLAC Laboratory Animal Co., Ltd (Chinese Academy of Sciences, Shanghai, China), the certificate number was SCXK (Shanghai) 2012-0002. The Huh-7 cells in logarithmic growth phase were injected subcutaneously into the right axilla ($5\times10^6$ cells/100 µl/mouse), ten days after inoculation, the tumor formation rate was 100%, and the diameter of the xenograft tumors was approximately 0.8-1.0 cm. The mice in every cell model were randomly divided into four groups (AdSVPE1a-LncR, AdSVPeGFP-LncR, Ad5-eGFP and blank control group), n=10 in each group. The virus treatment groups received the corresponding viruses via intratumoral injection at a dose of $2\times10^8$ pfu/100 µl/mouse, once every other day for a total of five times. The blank control group received saline injections at the same time (100 µl/mouse). After treatments, the tumor size was measured every week and the tumor volume was calculated as follows: maximum diameter×minimum diameter$^2$×0.5. A growth curve was then plotted.

The tumor growth rate of the AdSVPE1a-lncR treatment group was significantly slower than that of the blank control group at 14 days after treatment. At 21 days, the tumor volume started to decrease. The AdSVPeGFP-LncR group also had some growth inhibition at 28 days after treatment, and the difference was significant compared with the blank control group even though the tumor continued to grow. The Ad5-eGFP group did not show growth inhibition during the experiment (Table. 2). The observation continued to 42 days after treatment, and the tumor volume in the AdSVPE1a-lncR group was significantly smaller than that before treatment (FIG. 6). After finishing the observation, nude mice were euthanized.

TABLE 2

Antitumor effect of AdSVPE1a-LncR on Huh-7 xenografts in nude mice

| Time (day) | AdSVPE1a-LncR | | AdSVPeGFP-LncR | | Ad5-eGFP | | Blank Control |
|---|---|---|---|---|---|---|---|
| | Tumor Volume | *P | Tumor Volume | *P | Tumor Volume | *P | Tumor Volume |
| 0 | 306.76 ± 44.68 | 0.9270 | 305.51 ± 43.35 | 0.9777 | 293.77 ± 50.18 | 0.5914 | 304.98 ± 41.08 |
| 7 | 550.54 ± 70.89 | 0.1761 | 582.99 ± 97.13 | 0.4813 | 552.11 ± 140.25 | 0.2837 | 622.92 ± 146.28 |
| 14 | 918.83 ± 143.89 | 0.0153 | 1125.08 ± 256.37 | 0.4663 | 1103.17 ± 216.12 | 0.5774 | 1061.35 ± 87.18 |
| 21 | 903.50 ± 147.11 | 0.0000 | 1342.52 ± 352.92 | 0.2535 | 1408.94 ± 321.97 | 0.4407 | 1526.48 ± 344.44 |
| 28 | 813.20 ± 130.20 | 0.0000 | 1444.41 ± 504.63 | 0.0017 | 2120.32 ± 208.38 | 0.8118 | 2150.77 ± 339.68 |
| 35 | 470.10 ± 116.57 | 0.0000 | 1973.86 ± 355.62 | 0.0022 | 2624.40 ± 457.67 | 0.9621 | 2614.68 ± 443.41 |
| 42 | 241.20 ± 95.66 | 0.0000 | 2208.91 ± 560.62 | 0.0037 | 2969.63 ± 456.18 | 0.3482 | 3174.69 ± 495.17 |

Ps: *Compared with the control group at the same time, T-test.

The present invention has been described with some preferred embodiments thereof and it is understood that many changes and modifications in the described embodiments can be carried out without departing from the scope and the spirit of the invention that is intended to be limited only by the appended claims.

The invention claimed is:

1. An LncRNA that competitively consumes the carcinogenic microRNAs, wherein the LncRNA comprises n copies of SEQ ID NO.4 or is encoded by a coding sequence of n copies of SEQ ID NO.1, and wherein the n is an integer greater than or equal to 1.

2. An oncolytic adenovirus comprising an oncolytic adenovirus genome, wherein the oncolytic adenovirus genome comprises an expression cassette comprising the sequence of n copies of SEQ ID NO.1 of claim 1.

3. The oncolytic adenovirus of claim 2, wherein the expression cassette further comprises a promoter that regulates the expression of the LncRNA, wherein the promoter that regulates the expression of the LncRNA is inserted before transcriptional start sites of the LncRNA coding sequence.

4. The oncolytic adenovirus of claim 3, wherein the oncolytic adenovirus genome further comprises an essential virus proliferation gene and a tumor-selective promoter, wherein the tumor-selective promoter can regulate expression of the essential virus proliferation gene.

5. The oncolytic adenovirus of claim 4, wherein the oncolytic adenovirus is based on human adenovirus type 5, wherein the promoter that regulates the expression of the LncRNA comprises the sequence of SEQ ID NO.6, wherein the essential virus proliferation gene comprises the sequence of SEQ ID NO.8, and wherein the tumor-selective promoter comprises the sequence of SEQ ID NO.7.

6. The oncolytic adenovirus of claim 2, wherein the oncolytic adenovirus genome comprises the sequence of SEQ ID NO.10.

7. A drug preparation comprising the LncRNA of claim 1, or the oncolytic adenovirus of claim 2, wherein the drug preparation is used in treatment of tumor.

8. The drug preparation of claim 7, wherein expression of miR-21, miR-221/222, miR-224, miR-17-5p, miR-10b, miR106b, miR-151-5p, miR-155, miR-181a/181b, miR-184, miR-1 and miR-449a in the tumor is high.

9. A reagent preparation comprising the LncRNA of claim 1, or the oncolytic adenovirus of claim 2, wherein the reagent preparation is used in study of molecular mechanism of liver cancer cells and treatment of liver cancer.

* * * * *